(12) United States Patent
Lombardo et al.

(10) Patent No.: US 7,557,193 B2
(45) Date of Patent: Jul. 7, 2009

(54) GLYCOPEPTIDES DERIVED FROM PANCREATIC STRUCTURES, ANTIBODIES AND APPLICATIONS THEREOF IN DIAGNOSTICS AND THERAPEUTICS

(75) Inventors: Dominique Lombardo, Marseille (FR); Eric Mas, Marseille (FR); Marie-Odile Sadoulet, Marseille (FR); Laurence Panicot-Dubois, Canohes (FR); Jean-Paul Bernard, Marseille (FR)

(73) Assignees: Universite de la Mediterranee, Marseilles (FR); Institut National de la Sante et de la Recherche Medicale, Paris (FR)

( * ) Notice: Subject to any disclaimer, the term of this patent is extended or adjusted under 35 U.S.C. 154(b) by 75 days.

(21) Appl. No.: 10/593,859

(22) PCT Filed: Mar. 30, 2005

(86) PCT No.: PCT/FR2005/000771

§ 371 (c)(1),
(2), (4) Date: Sep. 22, 2006

(87) PCT Pub. No.: WO2005/095594

PCT Pub. Date: Oct. 13, 2005

(65) Prior Publication Data

US 2007/0172485 A1 Jul. 26, 2007

(51) Int. Cl.
*C07K 16/00* (2006.01)
(52) U.S. Cl. .................................. 530/388.1; 424/130.1
(58) Field of Classification Search ........................ None
See application file for complete search history.

(56) References Cited

U.S. PATENT DOCUMENTS 6,180,370 B1 * 1/2001 Queen et al. ................ 435/69.6

FOREIGN PATENT DOCUMENTS

WO    WO 94/20610    9/2004

OTHER PUBLICATIONS

Holmes et al. (Hybridoma, vol. 19, No. 6, p. 503, 2000).*
Takeda et al. (J. Cancer Res. Clin. Oncol., vol. 118(5), pp. 377-385, May 1992).*
Thirion et al. (European J. of Cancer Prevention, vol. 5(6), pp. 507-511, 1996) Abstract only.*
Lombardo, D. "Bile Salt-Dependent Lipase: Its Pathophysiological Implications", *Biochimica et Biophysica Acta*, May 8, 2001, pp. 1-28, vol. 1533.
Mas, E. et al. "The Oncofetal J28 Epitope Involves Fucosylated O-Linked Oligosaccharide Structures of the Fetoacinar Pancreatic Protein", *Glycobiology*, 1997, pp. 745-752, vol. 7, No. 6.
Panicot, L. et al. "The Formation of the Oncofetal J28 Glycotope Involves Core-2 β6-N-Acetylglucosaminyltransferase and α3/4-Fusosyltransferase Activities", *Glycobiology*, 1999, pp. 935-946, vol. 9, No. 9.
Reue, K. et al. "cDNA Cloning of Carboxyl Ester Lipase from Human Pancreas Reveals a Unique Proline-Rich Repeat Unit", *Journal of Lipid Research*, 1991, pp. 267-276, vol. 32.
Panicot-Dubois, L. et al. "Monoclonal Antibody *16D10* to the C-Terminal Domain of the Feto-Acinar Pancreatic Protein Binds to Membrane of Human Pancreatic Tumoral SOJ-6 Cells and Inhibits the Growth of Tumor Xenografts", *Neoplasia*, 2004, pp. 713-724, vol. 6, No. 6.

* cited by examiner

*Primary Examiner*—Larry R. Helms
*Assistant Examiner*—Meera Natarajan
(74) *Attorney, Agent, or Firm*—Saliwanchik, Lloyd & Saliwanchik

(57) ABSTRACT

The invention relates to a glycopeptide comprising between 1 and 40 repeated C-terminal polypeptides, with 11 amino acids, of BSDL or FAPP, whereby the aforementioned polypeptides are glycosylated and bear glycosylated epitopes giving rise to a specific immunological reaction with induced antibodies in a patient suffering from type 1 diabetes, and/or purified from biological fluids of human or animal origin or recombinant and produced by expression in a standard host cell comprising an enzymatic material necessary for priming a glycosylation, said host cell being genetically modified such as to comprise a gene coding for the aforementioned polypeptides and a gene coding for one or more enzymes selected from among glycosyltransferases and anti-glycopeptide antibodies. The invention also relates to the applications thereof in therapeutics and diagnostics.

27 Claims, 4 Drawing Sheets

Exp. 1

Exp. 2

Figure 1:
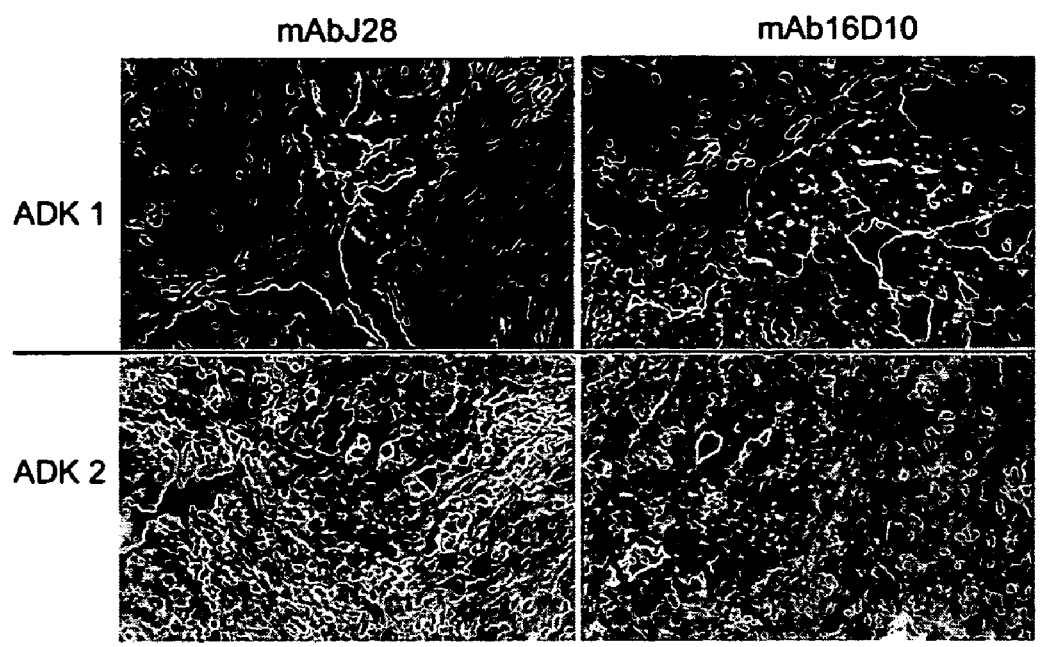

GLYCOPEPTIDES DERIVED FROM PANCREATIC STRUCTURES, ANTIBODIES AND APPLICATIONS THEREOF IN DIAGNOSTICS AND THERAPEUTICS

CROSS-REFERENCE TO RELATED APPLICATION

This application is the U.S. national stage application of International Patent Application No. PCT/FR2005/000771, filed Mar. 30, 2005, the disclosure of which is hereby incorporated by reference in its entirety, including all figures, tables and amino acid or nucleic acid sequences.

The invention relates to glycopeptides derived from pancreatic structures, antibodies and applications thereof in diagnostics and therapeutics.

More particularly, the invention relates to the obtaining of natural C-terminal glycopeptides of BSDL and/or FAPP carrying various glycosylated epitopes (alone or combined) recognized by induced antibodies in a patient suffering from type I diabetes and purified from biological fluids of human or animal origin as well as to said recombinant glycopeptides produced by biological engineering from cell lines containing cDNAs coding for the C-terminal peptides of FAPP and/or BSDL and cDNAs coding for the different glycosyltransferases required to build said glycopeptides. The invention also relates to monoclonal antibodies recognizing the recombinant and/or natural C-terminal glycopeptides of BSDL and/or FAPP, and to the use of said glycopeptides and said monoclonal antibodies as immunogenic agents, diagnostic agents and therapeutic agents that can be used for the diagnosis or the preventive or curative treatment of pancreatic pathologies such as diabetes and cancer of the exocrine pancreas or any other pathologies as well as in curative or preventive protocols of said pathologies.

Cancer of the exocrine pancreas, which accounts for over 20% of digestive tract cancers, is one of the most aggressive. In France for example, 4,000 new cases are diagnosed each year. Furthermore, its frequency is rising markedly in many regions of the world. Survival rates do not exceed 20% at 1 year and 3% at 5 years and mean survival is 3 to 4 months after diagnosis. The cancer is diagnosed late and progresses very rapidly, mainly through the formation of peritoneal and hepatic metastases. In addition, the deep anatomic location of the tumor, the absence of sensitive and specific early biological markers and its asymptomatic nature result in a diagnosis that always occurs late. Currently there are no effective therapies for exocrine pancreatic cancer, which is refractory to chemotherapy and radiation.

It would therefore be desirable to have specific markers of pancreatic cancer or other pancreatic pathologies available so as to diagnose these diseases and have products to provide effective treatments.

Now, after extensive research, and in a surprising manner, the applicants have discovered specific markers of pancreatic pathologies, and in particular of pancreatic cancer, expressed at the surface of the pancreatic tumor cell.

The applicants have discovered circulating antibodies directed against glycosylated antigenic structures of the C-terminal peptides of bile salt dependent lipase (BSDL), in diabetic patients.

The applicants have also discovered that monoclonal and polyclonal antibodies anti-glycosylated epitope expressed in the C-terminal part of human fetoacinar pancreatic protein (FAPP) specifically recognized human pancreatic tumor cell lines, but did not recognize tumor cell lines which were not of pancreatic origin.

The applicants have also discovered that monoclonal and polyclonal antibodies anti-glycosylated epitope expressed in the C-terminal part of human fetoacinar pancreatic protein (FAPP) specifically recognized human pancreatic tumor tissue, but did not recognize normal pancreatic tissue.

The applicants have further discovered that the antibodies anti-glycosylated epitope expressed in the C-terminal part of BSDL or FAPP could detect BSDL- and FAPP-derived glycopeptides in urine. In particular, the antibodies anti-glycosylated epitope expressed in the C-terminal part of FAPP could detect glycopeptides in urine allowing to identify a subject with a pancreatic pathology, particularly pancreatic cancer.

More particularly, therefore, the applicants have discovered that compounds having a glycopeptide structure whose peptide part is based on the repeated C-terminal sequences of BSDL, a digestive lipolytic enzyme present in normal pancreatic secretions, or based on the repeated C-terminal sequences of FAPP (an oncofetal form of BSDL) constituted such specific markers of pancreatic pathologies.

Indeed, BSDL and FAPP comprise repeated C-terminal peptide sequences of 11 amino acids, comprising a generally invariant part with 7 amino acids having the sequence Ala Pro Pro Val Pro Pro Thr and a glycosylation site. Said generally invariant part is flanked on either side by a glycine often substituted by a glutamic acid and contains the amino acids Asp and Ser on the N-terminal side.

The applicants have also discovered that the compounds having a glycopeptide structure which could be prepared by expression and secretion by a host cell, for example from Chinese hamster ovary (CHO), comprising a gene construct including a DNA molecule coding for one or more repeated sequences of the C-terminal peptide, particularly recombinant of BSDL, for example all or part of the 16 repeated sequences and also comprising a gene construct such as a DNA molecule coding for at least one enzyme with ose-transferase activity, in particular selected in the group consisting of Core 2 β(1-6) N-acetylglucosaminyltransferase, fucosyltransferase FUT3 which has α(1-3) and α(1-4) fucosyltransferase activity, or fucosyltransferase FUT7 which only has α(1-3) fucosyltransferase activity, constituted said specific markers of pancreatic cancer.

Thus the present application has as object a glycopeptide, particularly recombinant, possibly isolated or purified, comprising from 1 to 40 repeated C-terminal polypeptides, composed of 11 amino acids, of BSDL or FAPP, said polypeptides being glycosylated and carrying glycosylated epitopes giving rise to a specific immunological reaction with induced antibodies in a patient with type I diabetes and
    or else purified from biological fluids of human or animal origin
    or else recombinant and being produced by expression in a conventional host cell comprising an enzymatic machinery necessary for priming a glycosylation, said host cell being genetically modified so as to comprise a gene coding for said polypeptide and a gene coding for one or more enzymes selected from glycosyltransferases and in particular from Core2 β(1-6) N-acetylglucosaminyltransferase (abbreviated C2GnT), α(1-3) galactosyltransferase, fucosyltransferase 3 (abbreviated FUT3) and fucosyltransferase 7 (abbreviated FUT7).

In other preferred conditions of implementation of the invention, the aforementioned glycopeptide is essentially constituted of 1 to 40 glycosylated repeated C-terminal peptides, with 11 amino acids of BSDL or FAPP, and in particular exclusively constituted of said glycosylated peptides. Hence, the invention therefore relates to isolated, purified or recombinant glycopeptides comprising, or essentially consisting of, repetitions of the repeated C-terminal peptide sequence of 11 amino acids, preferably: D-S-G/E-A-P-P-V-P-P-T-G/E (SEQ ID No 14). Said glycopeptides can contain 1 to 40 repetitions. In a preferred embodiment, said glycopeptides comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 repetitions. Preferably, the glycopeptides comprise 1, 2, 3, 4, 5, 6, 7, 8, 9, 10, 11, 12, 13, 14, 15, 17, 18, 19, 20, 21, 22, 23, 24, 25, 26, 27, 28, 29, 30, 31, 32, 33, 34, 35, 36, 37, 38, 39 or 40 repetitions. In a particular embodiment, the glycopeptides comprise 1, 2, 3, 4, 5, 7, 8, 9, 10, 11, 12, 13, 14, 15, 17, 18, 19, 20, 21, 22, 23, 24, 25, 26, 27, 28, 29, 30, 31, 32, 33, 34, 35, 36, 37, 38, 39 or 40 repetitions. In another alternative embodiment, the glycopeptides comprise between 1 and 15 repetitions (for example, 1, 2, 3, 4, 5, 6, 7, 8, 9, 10, 11, 12, 13, 14, or 15 repetitions), preferably between 2 and 10 repetitions (for example, 2, 3, 4, 5, 6, 7, 8, 9, or 10 repetitions). In an additional embodiment, the glycopeptides comprise between 17 and 40 repetitions (for example, 17, 18, 19, 20, 21, 22, 23, 24, 25, 26, 27, 28, 29, 30, 31, 32, 33, 34, 35, 36, 37, 38, 39 or 40 repetitions). In preferred conditions of carrying out the invention, the aforementioned glycopeptide comprises from 1 to 40, preferably from 4 to 25 and more particularly from 6 to 16 repeated C-terminal polypeptides. In a particular embodiment, the glycopeptide comprises, or essentially consists of, 6 repetitions.

Preferably, the glycopeptides according to the invention are glycosylated by one or more enzymes having ose-transferase activity selected in the group consisting of Core 2 β(1-6) N-acetylglucosaminyltransferase (C2GnT), fucosyltransferase FUT3 which has α(1-3) and α(1-4) fucosyltransferase activity, or fucosyltransferase FUT7 which only has α(1-3) fucosyltransferase activity. In a particular embodiment, the glycopeptides according to the invention have been glycosylated by the enzymes C2GnT and FUT3. In an alternative embodiment, the glycopeptides according to the invention have been glycosylated by the enzymes C2GnT and FUT7. The invention also encompasses glycopeptides which have been glycosylated by the enzymes C2GnT, FUT3 and FUT7. In a preferred embodiment, the glycopeptides according to the invention have additionally been glycosylated by α(1-3)galactosyltransferase (GT). Thus, when the glycopeptide according to the invention is recombinant, the host cell which produces it comprises a gene coding for said polypeptide and a gene coding for one or more enzymes selected from glycosyltransferases and in particular from among C2GnT, FUT3 and FUT7. In a preferred embodiment, said host cell additionally comprises a gene coding for α(1-3)galactosyltransferase (GT).

In a particularly preferred embodiment, the invention relates to a recombinant, isolated or purified glycopeptide comprising 1 to 40 repetitions of the peptide sequence described in SEQ ID No 14 and glycosylated by one or more enzymes having ose-transferase activity selected in the group consisting of Core 2 β(1-6) N-acetylglucosaminyltransferase (C2GnT), fucosyltransferase FUT3 which has α(1-3) and α(1-4) fucosyltransferase activity, or fucosyltransferase FUT7 which has α(1-3) fucosyltransferase activity, said glycopeptide additionally being glycosylated by α(1-3)galactosyltransferase (GT).

"Isolated glycopeptides" is understood to mean that said compounds are separated from their natural environment. Thus, said compounds are separated from some or all of the other components of their natural environment.

"Purified glycopeptides" is understood to mean that said compounds are enriched in a mixture by at least approximately a factor of 1, preferably by at least 2, 3, 4 or 5-fold. The term "purified" does not necessarily mean that the compounds are absolutely pure. For instance, said compounds can have a purity of 30%, 40%, 50%, 60%, 70%, 80%, 90% or 100%. Preferably, however, said compounds generate only single bands in polyacrylamide gel electrophoresis.

Any suitable separation and/or purification method by which to obtain them can be used. In a particular embodiment, the glycopeptides are purified from a biological fluid from a human or animal subject. The biological fluid can be selected in the group consisting of serum, urine, pancreatic juices and milk secretions. Preferably, the biological fluid is urine. In a preferred embodiment, the subject is a patient who may be or who is suffering from a pancreatic disease, preferably pancreatic cancer. In another embodiment, the glycopeptides are purified from a cell culture. In an additional embodiment, the glycopeptides are purified from a tissue sample, preferably pancreatic tissue and in particular a pancreatic tissue tumor.

In the spirit of the application, the term "glycotype" refers to glycosylated epitopes. The glycosylated epitopes can involve one or more glycosylated chains. The term "mAb" ("Acm" in French) refers to a monoclonal antibody, the term "pAb" ("Acp" in French) to a polyclonal antibody.

In a particular embodiment, the invention relates to a glycopeptide according to the invention which can give rise to a specific immunological reaction with an antibody according to the invention. Preferably, the glycopeptide can give rise to a specific immunological reaction with one or more antibodies selected from J28 and 16D10. Optionally, the glycopeptide will give rise to a specific immunological reaction with J28. Alternatively, it will give rise to a specific immunological reaction with 16D10.

The host cells classically used in genetic engineering naturally contain enzymes, for example α-3 N-acetylgalactosaminyltransferase which adds an N-acetylgalactosamine generally on a serine or threonine residue of a peptide. For example this is the case for widely used host cells such as C127, COS, CHO or CHO-K1 which contain such enzymes.

In the present application and in that which follows, the term "conventional host cell" denotes a cell normally used for the production of glycopeptides, preferably a human cell or an animal cell such as C127, COS cells, or insect cells such as *Spodoptera frugiperda* ovary cells and particularly a CHO or CHO-K1 cell. Such a suitable conventional host cell can be selected in particular on the basis of its genetic machinery and its abilities to generate various glycosylated epitopes. To make said selection, an enzymatic assay can be carried out to detect the presence in particular of α-3 N-acetylglucosaminyltransferase in the host cell that one wishes to use.

The glycosyltransferases which are used can be of animal or preferably human origin.

In preferred conditions of implementation of the invention, the genetically modified conventional host cell comprises at least one gene coding for said polypeptide and at least one gene coding for Core2 β(1-6) N-acetylglucosaminyltransferase (C2GnT) and fucosyltransferase 3 (FUT3).

In other preferred conditions of implementation of the invention, particularly for applications in pancreatic cancer, the genetically modified conventional host cell comprises at least one gene coding for said polypeptide and at least one gene coding for Core2 β(1-6) N-acetylglucosaminyltransferase (C2GnT), fucosyltransferase 3 (FUT3) and α(1-3)galactosyltransferase (GT).

In still other preferred conditions of implementation of the invention, particularly for applications in type I diabetes, the genetically modified conventional host cell comprises at least one gene coding for said polypeptide and at least one gene coding for glycosyltransferase Core2 β(1-6) N-acetylglucosaminyltransferase (C2GnT) and fucosyltransferase 7 (FUT7).

All or part of the repeated C-terminal peptides can be glycosylated. Preferably, all of the repeated sequences will be glycosylated, generally 16 sequences, more specifically 6 sequences and in particular 2 sequences will be glycosylated.

The glycosylations can be due to one or more N-acetylglucosamine, N-acetylgalactosamine, sialic acid, glucose, galactose, fucose.

In yet other preferred conditions of implementation of the invention, the size of an aforementioned glycopeptide estimated by polyacrylamide gel electrophoresis (SDS-PAGE) is advantageously comprised between 20 and 120 kDa, preferably comprised between 20 and 85 kDa, more particularly comprised between 45 and 83 kDa.

In particular, the glycopeptides named C2-F3-16R, C2-F3-GT-6R and more particularly C2-F3-6R and C2-F7-16R are considered. C2-F3-16R designates a glycopeptide having 16 repetitions glycosylated by C2GnT and FUT3. C2-F3-GT-6R designates a glycopeptide having 6 repetitions glycosylated by C2GnT, FUT3 and GT. C2-F3-6R designates a glycopeptide having 6 repetitions glycosylated by C2GnT and FUT3. C2-F7-16R designates a glycopeptide having 16 repetitions glycosylated by C2GnT and FUT7. Preferably, the glycopeptides according to the invention are selected in the group consisting of C2-F3-6R, C2-F3-GT-6R, C2-F7-6R, C2-F7-GT-6R, C2-F3-F7-6R, and C2-F3-F7-GT-6R.

A cell line producing the glycopeptide C2-F7-16R was deposited with the Collection Nationale de Culture de Micro-organismes (CNCM) Institut Pasteur, 28, rue du Dr Roux, 75724 Paris Cédex 15, France on 16 Mar. 2004 under the number I-3189.

The person skilled in the art knows that a peptide can undergo several structural modifications without altering function.

The peptide can contain one or more modifications in its amino acids such as deletions, substitutions, additions or functionalizations such as acylation of amino acids, in so far as said modifications do not affect the immunologic characteristics thereof. In particular, the modification or modifications can be substitutions by a conservative amino acid (that is, having similar physicochemical characteristics). For example, in general, the substitution of a leucine residue by an isoleucine residue does not alter such properties. Generally, the modifications must concern less than 40%, in particular less than 30%, preferably less than 20% and more particularly less than 10% of the amino acids of the peptide. It is important that the modified peptide does not be denatured such as can be done for example by a physical treatment such as heat, so as to preserve the conformational sites thereof so that the antibodies induced by the modified derivatives will be active towards the native structure.

In general, with respect to the modifications, the homology or similarity between the aforementioned modified glycopeptide and the aforementioned native glycopeptide, as well as to the modes of use, or of coupling the immunogenic compound according to the invention to an immunogenic protein like tetanus toxoid, reference can be made in particular to WO-A-86/06414 or to EP-A-0.220.273 or else to PCT/US.86/00831, equivalent.

The glycopeptides which are the object of the invention can be prepared in particular from pancreatic juices, serum, milk, urine or amniotic fluid of human or animal origin. In a preferred embodiment, the glycopeptides according to the invention are isolated and/or purified from urine of human or animal origin. Preferably, the urine is of human origin. In a preferred embodiment, the urine is from a patient who may be or who is suffering from a pancreatic pathology. Preferably, the pancreatic pathology is pancreatic cancer. Those skilled in the art are familiar with the techniques that can be used to purify and/or isolate the inventive glycopeptides. In particular, the glycopeptides can be purified by using for example, but without being limited to said methods, centrifugations, ultrafiltrations, concentration steps, liquid chromatography on exclusion or affinity columns, reverse phase chromatography or cation or anion exchange chromatography, electrophoresis or a combination of said techniques. In particular, the antibodies specific of the glycopeptides according to the invention such as J28 and 16D10 can be used for an affinity purification. An example of a purification protocol is described in Experiment 7. Thus, the invention relates to a method of preparation of a glycopeptide according to the invention comprising collecting the urine of a subject and purifying said glycopeptide from the urine.

The invention more particularly relates to glycopeptides according to the invention which are purified and/or isolated from the urine of a patient who may be or who is suffering from a pancreatic pathology, in particular pancreatic cancer. As described hereinbelow, said purified glycopeptides can be used for preventive or therapeutic treatment by immunotherapy. For instance, they can be used to prepare a pharmaceutical and/or vaccine composition.

The inventive glycopeptides can be recombinant and prepared as follows.

A suitable conventional host cell line like CHO-K1 is transfected with a plasmid comprising the complementary DNA of the desired transferase or by plasmids comprising the complementary DNAs of the desired transferases, for example the glycosyltransferase Core2 β(1-6) N-acetylglucosaminyltransferase (C2GnT), fucosyltransferase 3 (FUT3), fucosyltransferase 7 (FUT7) or α(1-3)galactosyltransferase (GT), by using lipofectamine for example.

The resulting cell line is transfected with a plasmid enabling the expression and preferably the secretion of the recombinant peptides, for example a pSecTag plasmid containing the cDNA coding for an inventive glycopeptide, for example the C-terminal domain of BSDL or FAPP. SEQ ID Nos 6, 8, 10 and 12 are examples of sequences coding for a glycopeptide according to the invention.

The recombinant glycopeptide obtained by culturing the cell line containing the desired cDNAs is then advantageously purified for example on a polyacrylamide gel or by liquid and/or affinity chromatography and if desired it is analyzed by SDS-PAGE for identification.

Of course it is possible to transfer the genes required to prepare the inventive glycopeptides into the host cell by any other suitable method.

In preferred conditions of implementation of the aforementioned method, a suitable cell line like CHO-K1 is transfected with a plasmid comprising the complementary DNA of glycosyltransferase Core2 β(1-6) N-acetylglucosaminyltransferase (C2GnT), fucosyltransferase 3 (FUT3), and a glycopeptide according to the invention, for example the C-terminal polypeptide domain of FAPP or in particular of BSDL, preferably in that order.

In an advantageous manner, the CHO cell line and in particular the CHO-K1 cell line is used as host cell.

In an advantageous manner, the plasmids pSecTag, pcDNA-3 or pBK-CMV are used as plasmid.

More generally, the invention also has as object a method of preparation of a glycopeptide such as described hereinabove, characterized in that one transfers into a conventional host cell comprising an enzymatic machinery necessary for priming a glycosylation, a gene coding for the polypeptide according to the invention and at least one gene coding for one or more enzymes selected from glycosyltransferases, in conditions enabling the expression and optionally the secretion of the desired glycopeptide, and one isolates the expected glycopeptide.

The glycopeptides according to the invention, and in particular the natural or derivative glycopeptides of FAPP or BSDL, can be prepared from proteins isolated from biological fluids or tissues of any human or animal origin whatsoever, particularly sera, urine, pancreatic juices, milk secretions, tissue or cell homogenates, and the like, by chromatographic methods such as described by Lombardo et al. 1978, Biochim. Biophys. Acta, 527: 142-149, or by Abouakil et al. 1988, Biochim. Biophys. Acta, 961: 299-308, or by Wang & Johnson, 1983, Anal. Biochem., 133: 457-461 or else by Blackberg & Hernell, 1981, Eur J. Biochem. 116: 221-225. The homogeneous proteins are then hydrolyzed either by enzymatic methods involving any enzyme particularly proteolytic, or by chemical methods.

The natural glycopeptides can be isolated by chromatographic methods (gel filtration, affinity and immunoaffinity, ion exchange, etc.) as described in particular in Mas et al. 1997, Glycobiology, 7: 745-752, or Wang et al. 1995, Biochemistry, 34: 10639-10644, or by any other method.

Said glycopeptides can also be purified, isolated either directly from biological fluids or tissues as indicated earlier or subsequent to the aforementioned enzymatic or chemical treatments of said biological fluids or tissues.

The glycosylation of said natural glycopeptides of BSDL or FAPP can be modified by any chemical or enzymatic routes (use of native, soluble recombinant, membranar in particular, of glycosidases or glycosyltransferases) in order to obtain the glycan structures hereinbelow used in particular for the diagnosis of the pathologies indicated hereinabove and hereinbelow or for vaccination against said pathologies, or for obtaining or producing antibodies which are the object of the invention.

In addition, it is possible to modify the peptide sequence of the natural or recombinant glycopeptides of the invention.

The natural and particularly recombinant, isolated or purified glycopeptides which are object of the invention have very interesting properties. In particular, they exhibit remarkable immunogenic properties, specific of pancreatic pathologies.

Said properties are illustrated hereinbelow in the experimental section. They justify the use of the aforementioned glycopeptides as medicament.

This is why the invention also has as object the aforementioned glycopeptides, for the use thereof in a method of therapeutic treatment of the human or animal body, that is to say, as medicament.

The medicaments according to the invention can be used for example in immunotherapy (immunization, vaccination) preventive and/or curative treatment of pancreatic cancer, breast cancer, for cell-based immunotherapy: autologous vaccination by activation of the patient's immune system (dendritic or other cells, etc.), for the diagnosis of certain pathologies such as type I diabetes by detection of circulating antibodies directed against said structures in patients afflicted with a diabetic pathology and more generally with any other pathology requiring the use of one or more of said glycopeptides.

They can also be used in other biological systems such as inflammation, the formation of metastases and the inhibition of invasion by pathogens.

Thus, the invention relates to a pharmaceutical or vaccine composition comprising a glycopeptide according to the invention. In particular, the invention relates to a pharmaceutical or vaccine composition comprising a glycopeptide comprising 1 to 40 repetitions of the peptide sequence described in SEQ ID No 14 and glycosylated by one or more enzymes having ose-transferase activity selected in the group consisting of Core 2 $\beta(1-6)$ N-acetylglucosaminyltransferase (C2GnT), fucosyltransferase FUT3 which has $\alpha(1-3)$ and $\alpha(1-4)$ fucosyltransferase activity, or fucosyltransferase FUT7 which has $\alpha(1-3)$ fucosyltransferase activity. Optionally, said glycopeptide is glycosylated by the enzymes C2GnT and FUT3. Optionally, said glycopeptide is glycosylated by the enzymes C2GnT and FUT7. Optionally, said glycopeptide is glycosylated by the enzymes C2GnT, FUT3 and FUT7. Preferably, said glycopeptide is further glycosylated by $\alpha(1-3)$galactosyltransferase (GT). In a preferred embodiment, said glycopeptide comprises between 1 and 15 of said repetitions. Said glycopeptide can be recombinant or purified from a biological fluid. Preferably, said biological fluid is urine, in particular urine from a subject suffering from a pancreatic pathology, particularly pancreatic cancer. In a particular embodiment, said glycopeptide is loaded on antigen-presenting cells, preferably dendritic cells.

The invention also relates to the use of a glycopeptide or a pharmaceutical or vaccine composition according to the invention as medicament. In particular, the invention relates to the use of a glycopeptide or a pharmaceutical or vaccine composition according to the invention for preparing a medicament intended for the preventive or curative treatment of a disease selected in the group consisting of a cancer, an inflammatory disorder, a vascular pathology or an infection by a pathogen. Preferably, the disease is a breast or pancreas cancer. In a preferred embodiment, the invention relates to the use of a glycopeptide or a pharmaceutical or vaccine composition according to the invention for preparing a medicament intended for the treatment or prevention of a pancreatic pathology, in particular pancreatic cancer. In a preferred embodiment, the glycopeptide is obtained by purification from the urine of a subject suffering from a pancreatic pathology, preferably pancreatic cancer.

Within an adjuvant formulation, the immunogen, in this case a glycopeptide according to the invention, can be included in particular in a water-in-oil emulsion, by using ISA 51 for example.

A vaccine preparation containing the immunogenic glycopeptide can be administered in a suitable pharmaceutical formulation to induce an immune response of the systemic type by the intramuscular (im), subcutaneous (sc), intradermal (id) route or of the mucosal type by the intranasal, oral, vaginal or rectal route.

A vaccine preparation containing the immunogenic glycopeptide can also contain other immunogens.

A systemic pharmaceutical preparation, administered by the sc, im, id route, can be a water-in-oil emulsion containing the immunogenic glycopeptide, or an immunogen-embedded calcium phosphate suspension, or aluminium hydroxide adsorbing the immunogen.

The vaccine preparations can be formulated for the intranasal route in the form of a gel with carbopol as excipient, nose drops or spray and for the oral route in the form of gastroresistant capsules, gastroresistant granules or sugar coated tablets.

The usual dose, which varies according to the subject and the causal pathology, can be for example from 1 to 100 mg of a glycopeptide according to the invention, in particular of the glycopeptide described in example 4 hereinbelow, administered by the systemic route in humans, every two weeks for 10 to 20 weeks.

The invention also has as object pharmaceutical compositions which contain at least one aforementioned glycopeptide, as active ingredient.

In said compositions, the active ingredient is advantageously present at physiologically effective doses; in particular the aforementioned compositions contain an effective vaccine dose of at least one aforementioned active ingredient.

As medicaments, the glycopeptides described hereinabove can be incorporated in pharmaceutical compositions intended for the digestive or parenteral route.

For example, said pharmaceutical compositions can be solids or liquids and be supplied as pharmaceutical formulations commonly used in human medicine, such as for example simple or sugar-coated tablets, capsules, granules, caramels, suppositories, particularly injectable preparations; they are prepared by the usual methods. The active ingredient(s) can be formulated therein with excipients usually employed in said pharmaceutical compositions, such as talc, gum arabic, lactose, starch, magnesium stearate, cocoa butter, vehicles which are aqueous or not, animal or vegetable fats, paraffin derivatives, glycols, various wetting agents, dispersives or emulsifiers, preservatives.

The invention also has as object a method of preparation of a composition such as described hereinabove, characterized in that the active ingredient(s) are mixed with acceptable excipients, particularly pharmaceutically acceptable, according to established methods.

The invention further has as object the use of a glycopeptide such as described hereinabove, for preparing a medicament intended for the curative or preventive treatment of pancreatic cancer or breast cancer or other pathologies such as a vascular pathology or angiogenesis.

The invention further relates to a method of preventive or curative treatment of a disease selected in the group consisting of a cancer, an inflammatory disorder, a vascular pathology or an infection by a pathogen in a subject, comprising administering an effective dose of a glycopeptide according to the invention.

In a preferred embodiment of cancer treatment, in particular prostate cancer, the glycopeptide can be loaded on an allogeneic antigen-presenting cell. Preferably, the antigen-presenting cell is a dendritic cell. In a preferred manner, the antigen-presenting cell is autologous, that is, it has previously been removed from the recipient subject or it is derived from stem cells originating from the recipient subject. In an alternative, the antigen-presenting cell originates from a sample taken from an allogeneic subject, that is to say, compatible with the recipient. Thus, in this embodiment, the pharmaceutical or vaccine composition according to the invention comprises antigen-presenting cells loaded or "pulsed" with a glycopeptide according to the invention. The invention therefore relates to the use of a pharmaceutical or vaccine composition comprising antigen-presenting cells loaded or "pulsed" with a glycopeptide according to the invention as medicament, in particular as medicament for the treatment or prevention of breast or pancreatic cancer, preferably pancreatic cancer. In a preferred embodiment, the glycopeptide is obtained by purification from the urine of a subject suffering from a pancreatic pathology, preferably pancreatic cancer. In a most desirable embodiment, the glycopeptide is obtained by purification from the urine of a treated subject. Preferably, the subject is human. The invention also relates to a method of curative or preventive treatment of a pancreatic pathology, preferably pancreatic cancer, or breast cancer, comprising: providing the glycopeptides according to the invention; and administering said glycopeptides, optionally loaded on antigen-presenting cells, said administration allowing to treat, attenuate or prevent a pancreatic pathology, preferably pancreatic cancer, or breast cancer. In a preferred embodiment, the treated disease is pancreatic cancer. Said glycopeptides can be recombinant or isolated from a biological sample, preferably a biological fluid. In a preferred embodiment, said glycopeptides are isolated and/or purified from the urine of a subject suffering from a pancreatic pathology, preferably pancreatic cancer, or breast cancer. Preferably, said glycopeptides are isolated and/or purified from the urine of a treated subject. Thus, the step of providing the glycopeptides can comprise the collection of the biological fluid, preferably urine, and the purification of said glycopeptides.

The properties of the glycopeptides described hereinabove also justify their use in diagnosis, particularly in immunoenzymatic methods.

This is why the invention also has as object a composition for the diagnosis in vitro of the presence of an antibody directed against a glycopeptide described hereinabove, in a human biological sample, characterized in that it contains at least one glycopeptide such as described hereinabove.

The invention also has as object a method for the detection in vitro of the presence of induced antibodies in a human subject suffering from an aforementioned pathology, in a human biological sample such as serum and, more particularly, for the diagnosis in vitro of pancreatic cancer or a diabetic pathology and originating from the person who is the object of the diagnosis, characterized in that said biological sample is contacted with an antigen recognized by an induced antibody in the patient such as defined hereinabove or hereinbelow, in conditions allowing the formation of an immunological complex between said antigen and said antibody and in that the immunological complex possibly formed between said antibody and antigen is detected.

The invention also has as object the necessary materials or kit for the detection of induced antibodies in a human subject suffering from an aforementioned pathology, in a biological sample, particularly a possible carrier of said antibodies, characterized in that it comprises:

at least one glycopeptide such as described hereinabove means for detecting the immunological complex resulting from the immunological reaction between the antigen and said biological sample.

The glycopeptides, particularly recombinant, isolated or purified which are the object of the invention can also be used in the diagnosis of certain pathologies such as type I diabetes by detection of circulating antibodies directed against these structures in patients with such diabetic pathology.

In particular, the glycopeptides named C2-F7-16R are used for the diagnosis of type I diabetes.

As the glycopeptides, particularly recombinant, isolated or purified which are the object of the invention possess very interesting antigenic properties, they also enable the production of antibodies particularly monoclonal.

Hence the application also has as object an antibody particularly monoclonal giving rise to a specific immunological reaction with a glycopeptide such as described hereinabove, with the exception of antibody J28 and any other antibody meeting the hereinabove definition and which can be described in the literature. The monoclonal antibodies can be from any class, in particular IgM, IgD, IgE or IgA. Preferably, the monoclonal antibodies are IgG. An antibody according to the invention can be modified, regardless of the initial class thereof, to an antibody from another immunoglobulin class, for example by known molecular biology methods (Lewis et al., 1992, Hum. Antibodies Hybridomas, 3: 146-52; Lewis et al., 1993, J. Immunol., 151: 2829-38; Hall et al., 1994, Cancer Res., 54: 5178-85; Shepherd & Dean, Monoclonal Antibodies, Oxford University Press, 2000, 479 pages). These same monoclonal antibodies can be humanized by genetic recombination or by any other method in order to conserve their recognition site for said recombinant or natural glycopeptides so as to use them in the conditions indicated earlier.

In particular an antibody obtained by immunization of a mammal with the aid of a glycopeptide such as described hereinabove, is chosen.

More particularly, the invention relates to the antibodies described in the examples and in particular the 16D10 antibodies of the IgM type which can be produced by the hybridoma deposited with the Collection Nationale de Culture de Microorganismes (CNCM), Institut Pasteur, 28, rue du Dr Roux, 75724 Paris Cédex 15, France on 16 Mar. 2004 under the number I-3188 and 8H8 of the IgG type.

Preferably, the invention relates to a monoclonal antibody selected in the group consisting of the monoclonal antibody 16D10, a fragment or derivative thereof, and an antibody which essentially binds to the same epitope as monoclonal antibody 16D10. Optionally, said antibody is humanized, chimeric or human. Preferably, the antibody is of the IgG type. Optionally, the antibody is a single chain antibody.

An antibody fragment or derivative is understood to mean an entity conserving substantially the same specificity as the antibody in question. A fragment thereof can be a Fab, Fab', F(ab)2 and sFv fragment (Blazar et al., 1997, Journal of Immunology 159: 5821-5833 and Bird et al., 1988, Science 242: 423-426). Fv, Fab, or F(ab)2 fragments according to the invention can be obtained by classical enzymatic digestion methods. A derivative thereof can be a chimeric, humanized or single chain scFv antibody. Said derivatives can be obtained by classical genetic engineering methods. Polynucleotides coding for variable regions of antibody 16D10 can be obtained for example by cloning said variable regions from a 16D10-antibody-producing hybridoma cDNA library. They can also be totally or partially prepared by nucleic acid synthesis, based on the nucleotide sequences of said variable regions. For example polynucleotides coding for the CDRs of 16D10 can be synthesized, and incorporated into suitable regions of an other antibody, in particular an antibody of human origin and/or of the IgG type, by known techniques of CDR grafting, such as those described by Routledge et al. ("Reshaping antibodies for therapy", in Protein Engineering of Antibody Molecules for Prophylactic and Therapeutic Applications in Man, 13-44, Academic Titles, Nottingham England (1993)] or by Roguska et al., 1996, Protein Engineering, 9 (10): 895-904).

The invention also has as object any nucleic acid molecule coding for a protein comprising the CDRs of antibody 16D10, and any recombinant vector, in particular any expression vector, comprising said nucleic acid molecule, any host cell comprising said nucleic acid or said vector.

The invention also has as object a method of preparation of an anti-glycopeptide antibody such as described hereinabove, characterized in that a mammal is immunized with the aid of said glycopeptide or with the aid of a mixture of FAPP and BSDL isolated from any human or animal biological tissue or fluid and in particular normal and pathological human pancreatic juices and the expected antibodies recognizing the C-terminal domain of said proteins are then recovered and purified if so desired.

The application equally has as object a method of preparation of an anti-glycopeptide antibody such as described hereinabove characterized in that one clones B lymphocytes originating from a subject immunized with the aid of a natural or recombinant glycopeptide such as described hereinabove or with the aid of a mixture of FAPP and BSDL such as described hereinabove and transformed by Epstein-Barr virus (EBV), then recovers the expected antibodies secreted by said transformed B lymphocytes.

In particular, the monoclonal antibodies object of the invention can give rise to a specific immunological reaction with a glycopeptide such as described hereinabove.

In a particular embodiment of the invention, the antibody essentially binds to the same epitope as the monoclonal antibody 16D10 or J28 (respectively produced by hybridoma 16D10 or J28). Preferably, said antibody is a monoclonal antibody. Preferably, the invention relates to the monoclonal antibody 16D10 (produced by hybridoma 16D10), but it shall be understood that the invention also relates to monoclonal antibodies which can specifically compete with antibody 16D10. Likewise, in a particular embodiment, the monoclonal antibodies according to the invention can specifically compete with antibody J28.

The term "essentially binds to the same epitope or determinant as" an antibody of interest means that the antibody "competes" with said antibody of interest. The term "essentially binds to the same epitope or determinant as" an antibody of interest does not mean that the two antibodies have exactly the same epitope. However, in a particular embodiment, the two antibodies can have the same epitope. The term "essentially binds to the same epitope or determinant as" monoclonal antibody 16D10 means that the antibody "competes" with antibody 16D10. Generally, an antibody which "essentially binds to the same epitope or determinant as" an antibody of interest (e.g., antibody 16D10) means that the antibody "competes" with said antibody of interest for a glycopeptide according to the invention, in particular one or more proteins selected from BSDL or FAPP or a fragment thereof, preferably a C-terminal part of BSDL or FAPP as described herein, even more preferably a part comprising one or more repetitions of 11 amino acids of BSDL or FAPP, or a part or fragment of same. In other examples, an antibody essentially binds to the same epitope or determinant of BSDL or FAPP when the antibody "competes" with the antibody of interest for binding to BSDL or FAPP.

The term "essentially binds to the same epitope or determinant as" an antibody of interest means that the antibody "competes" with said antibody of interest for any BSDL and/or FAPP molecule to which said antibody of interest specifically binds. The term "essentially binds to the same epitope or determinant as" monoclonal antibody 16D10 means that the antibody "competes" with said monoclonal antibody 16D10 for any BSDL and/or FAPP molecule to which said monoclonal antibody 16D10 specifically binds. For example, an antibody which essentially binds to the same epitope or determinant as monoclonal antibodies 16D10 or J28 "competes" with said antibodies 16D10 or J28 for binding to BSDL or FAPP, respectively.

The identification of one or more antibodies which essentially bind(s) to the same epitope as the monoclonal antibodies described herein can be carried out by using any immunological screening method in which a competition between antibodies can be evaluated. Many assays are routinely carried out and are well known to those skilled in the art (see for example U.S. Pat. No. 5,660,827 granted 26 Aug. 1997, which is specifically incorporated herein by reference). The determination of the epitope to which an antibody binds is not necessary to identify an antibody which binds, or which essentially binds, to the same epitope as the monoclonal antibody described herein.

For example, when the candidate antibodies to be studied have been obtained from different animal sources, or possibly have different Ig isotypes, a simple competition assay can be employed wherein the control antibody (antibody 16D10 for example) and the candidate antibody are mixed (or pre-adsorbed) and contacted with a sample containing either BSDL or FAPP, both known to bind to antibody 16D10. Protocols based on ELISA, radioimmunological assays, western blot analyses, or the use of a BIACORE analysis (as described, for example, in the Examples) are suitable for use in simple competition tests.

In particular embodiments, it is possible to first prepare mixtures of control antibodies (for example, antibody 16D10) with variable amounts of candidate antibodies (for example, approximately 1:10 or approximately 1:100) before contacting with the BSDL or FAPP antigen sample. In another embodiment, the control antibody and the variable amounts of candidate antibodies can simply be mixed at the time of contact with the BSDL or FAPP antigen sample. So long as one can distinguish bound antibodies from free antibodies (for example, by using separation methods or by washing to remove unbound antibodies) and distinguish antibody 16D10 from the candidate antibodies (for example, by using secondary antibodies specific of the species or the isotype or by labelling antibody 16D10 with a detectable tag), it will be possible to determine if the candidate antibodies reduce the binding of antibody 16D10 to the BSDL or FAPP antigen, thereby indicating whether the candidate antibody essentially recognizes the same epitope as antibody 16D10. The binding of the control antibody in the presence of a completely irrelevant antibody can serve as an upper control value. The lower control value can be obtained by incubating the labelled control antibody (16D10) with unlabelled antibodies recognizing exactly the same epitope (16D10), in this way inducing a competition which reduces the binding of the labelled antibody. In one test, a significant reduction in the reactivity of a labelled antibody in the presence of a candidate antibody indicates that the candidate antibody essentially recognizes the same epitope, that is to say, it cross-reacts with the labelled antibody (16D10). Any candidate antibody which reduces the binding of antibody 16D10 to each of the antigens BSDL or FAPP by at least approximately 20%, 30%, 40%, 50%, preferably by at least about 60%, or even more preferably by at least about 70% (for example, 65-100%), at a ratio of 16D10 antibody to candidate antibody of between about 1:10 and about 1:100, is considered to be an antibody which essentially binds to the same epitope or determinant as antibody 16D10. Preferably, said candidate antibodies reduce the binding of antibody 16D10 to the BSDL or FAPP antigen by at least about 90% (for example, about 95%). Preferably, antibody 16D10 also reduces the binding of the candidate antibody to the BSDL or FAPP antigen when the binding is evaluated in the same way, although the degree of reduction in binding may be different.

The competition can be evaluated by a flow cytometry assay for example. In such assay, cells carrying a BSDL or FAPP antigen, for example cells transfected with BSDL or FAPP, are first incubated with antibody 16D10, for example, then with the candidate antibody labelled with a fluorochrome or with biotin. The antibody is considered to compete with antibody 16D10 if the binding observed after preincubation with a saturating amount of 16D10 is about 30%, preferably about 40% about 50%, about 80%, or more (for example, about 90%) of the binding observed (as measured by fluorescence) with the antibody without preincubation with 16D10. Alternatively, an antibody is considered to compete with antibody 16D10 when the binding observed with labelled 16D10 antibody (labelled with a fluorochrome or biotin) in cells preincubated with a saturating amount of the candidate antibody is about 80%, preferably about 50%, about 40%, about 30%, or less (for example, about 20%) of the binding observed without preincubation with the antibody.

In an advantageous manner, a simple competition assay in which a candidate antibody is preabsorbed and applied at a saturating concentration on a surface on which a BSDL or FAPP antigen has been immobilized can also be used. The surface in the simple competition assay is preferably a BIACORE chip (or another support compatible with surface plasmon resonance analysis). The control antibody (for example, 16D10) is then contacted with a surface at a saturating concentration of BSDL or FAPP and binding of the control antibody to the surface carrying BSDL or FAPP is measured. Said binding of the control antibody is compared with the binding of the control antibody to the surface carrying BSDL or FAPP in the absence of the candidate antibody. In an assay test, a significant reduction in binding of the control antibody to the surface carrying BSDL or FAPP in the presence of the candidate antibody indicates that the candidate antibody essentially recognizes the same epitope as the control antibody in such a way that the candidate antibody cross-reacts with the control antibody. Any candidate antibody which reduces the binding of the control antibody (such as antibody 16D10) to the BSDL or FAPP antigen by at least about 30% or preferably about 40% can be considered an antibody which essentially binds to the same epitope as the control antibody (for example, 16D10). Preferably, said candidate antibody reduces the binding of the control antibody (for example, 16D10) to the BSDL or FAPP antigen by at least about 50% (for example, at least about 60%, at least about 70%, or more). It shall be understood that the order between the control and candidate antibodies can be reversed, that is to say, that the control antibody can be the first to bind to the surface and that the candidate antibody is subsequently contacted with the surface in a competition test. Preferably, the antibody displaying the highest affinity for BSDL or FAPP is bound to the surface carrying BSDL or FAPP first, since it is hoped that the reduction in binding observed with the second antibody (presuming that the antibodies cross-react) will be of greater amplitude. Other examples of such tests are described in the examples and in Saunal and Regenmortel, (1995, J. Immunol. Methods 183: 33-41, the content thereof being incorporated herein by reference).

Said properties are illustrated in the experimental section which follows. They justify the use of the monoclonal antibodies described hereinabove and in particular of the monoclonal antibodies 8H8, 16D10, 14H10 and other monoclonal antibodies directed against the C-terminal part of BSDL or FAPP, for the diagnosis, prognosis and/or prediction of several pancreatic pathologies including pancreatic cancer, pancreatitis and type I diabetes, but also breast cancer or cardiovascular diseases. The diagnostic information can be obtained from serum and/or urine assays.

The antibody 16D10 has particularly interesting properties. In fact, it is specific of pancreatic cancer. It recognizes neither normal tissues nor other types of tumor tissues. The epitope recognized by antibody 16D10 is different from that recognized by antibody J28 because these two antibodies do not compete. These results are described in example 4.

Thus, the invention relates to a method enabling the detection, preferably in vitro, of a pancreatic pathology, in particular pancreatic cancer, comprising contacting a biological sample with an antibody according to the invention and detecting the formation of immunological complexes resulting from the immunological reaction between said antibody and said biological sample. Preferably, the antibody is the antibody 16D10, a fragment or derivative thereof, or an antibody which essentially binds to the same epitope or determinant as the former. Preferably, the biological sample is a sample of pancreatic tissue (biopsy) or a biological fluid. The biological sample can be a tissue slice (immunohistochemistry) or cells contained in the sample or derived by culturing the sample (immunocytochemistry). The biological fluid can be selected in the group consisting of serum, urine, pancreatic juices and milk. Preferably, the biological fluid is urine. The complex can be detected directly by labelling the antibody according to the invention or indirectly by adding a molecule which reveals the presence of the antibody according to the invention (secondary antibody, streptavidin/biotin tag, etc.). For example, labelling can be accomplished by coupling the antibody with radioactive or fluorescent tags. These methods are well known to those skilled in the art.

The invention also relates to the use of an antibody according to the invention for preparing a diagnostic composition that can be used for detecting a pancreatic pathology in vivo or in vitro. Preferably, the antibody is the antibody 16D10, a fragment or derivative thereof, or an antibody which essentially binds to the same epitope or determinant as the former. Preferably, the pancreatic pathology is pancreatic cancer.

In a preferred embodiment, the invention relates to a method enabling the detection of a pancreatic pathology in a subject, in particular pancreatic cancer, comprising recovering the urine of the subject, contacting said urine with an antibody according to the invention, and detecting the formation of immunological complexes resulting from the immunological reaction between said antibody and said urine. Preferably, the antibody is the antibody 16D10, a fragment or derivative thereof, or an antibody which essentially binds to the same epitope or determinant as the former. The antibody can also be the antibody J28, a fragment or derivative thereof, or an antibody which essentially binds to the same epitope or determinant as the former. Preferably, the pancreatic pathology is pancreatic cancer. The complex can be detected directly by labelling the antibody according to the invention or indirectly by adding a molecule which reveals the presence of the antibody according to the invention (secondary antibody, streptavidin/biotin tag, etc.). These methods are well known to those skilled in the art. Optionally, the method can comprise intermediate steps of treating the urine sample before incubation with said antibody. For example, said steps can comprise concentration of the urine, steps of glycopeptide enrichment or purification, and the like.

The invention also relates to the use of an antibody according to the invention for the diagnosis of a pancreatic pathology, in particular pancreatic cancer in a subject. Preferably, the antibody is antibody 16D10, a fragment or derivative thereof, or an antibody which essentially binds to the same epitope or determinant as the former. The antibody can also be antibody J28 a fragment or derivative thereof, or an antibody which essentially binds to the same epitope or determinant as the former.

The invention relates to a diagnostic kit for a pancreatic pathology, in particular pancreatic cancer, comprising an antibody according to the invention. Said kit can additionally comprise means by which to detect the immunological complex resulting from the immunological reaction between the biological sample and said antibody, in particular reagents enabling the detection of said antibody. In a particular embodiment, the kit comprises the antibody 16D10, a fragment or derivative thereof, or an antibody which essentially binds to the same epitope or determinant as the former.

These properties justify the use of the monoclonal antibodies described hereinabove for developing new therapeutic protocols for cancer of the exocrine pancreas such as targeting tumor cells with said antibodies coupled with drugs (chemotherapy) or radioactive elements (radiotherapy and radiodiagnosis) or else with genes modifying the outcome or behavior of the neoplastic cells (gene therapy).

The antibodies coupled with radioactive elements can be used in radiolocalization (immunoscintigraphy) of primary tumors and metastases (secondary tumors).

Said diagnostic information can be acquired in serum and/or urine assays.

In particular, the invention relates to antibodies according to the invention, in particular monoclonal, coupled with an antitumoral active substance, which can be used in the treatment of pancreatic cancer to target and destroy pancreatic tumor cells.

Similarly, radioactive elements (or others) can be coupled with said antibodies and allow a precise localization of primary tumors and metastases. Said antibodies can also make is possible to clearly and accurately differentiate normal tissue from tumor tissue.

These same properties justify the use of said monoclonal antibodies alone, combined or coupled with a diagnostic or therapeutic molecule to develop new passive immunotherapy protocols for the aforementioned pathologies.

Thus the invention also has as object a composition for the in vitro diagnosis of a pathology such as described hereinabove, in a human biological sample, characterized in that it contains at least one monoclonal antibody such as described hereinabove, in particular coupled with at least one radioactive element. Depending on the nature of the radioactive element, said composition can be used curatively to irradiate a region of the pancreas.

As a diagnostic composition, the aforementioned antibodies can be mixed with acceptable excipients.

The invention also has as object a kit for detecting the presence of a glycopeptide such as described hereinabove appearing in a human subject afflicted with a diabetic or neoplastic pathology in a human biological sample originating from the individual to be diagnosed, characterized in that it comprises:
at least one antibody such as described hereinabove,
means for detecting the immunological complex resulting from the immunological reaction between the antibody and the biological sample.

The preferred conditions of employing the glycopeptides and antibodies described hereinabove also apply to the other objects of the invention mentioned earlier, in particular to the diagnostic methods.

The invention also relates to a pharmaceutical composition comprising an antibody according to the invention. Preferably, the antibody is the antibody 16D10, a fragment or derivative thereof, or an antibody which essentially binds to the same epitope or determinant as the former. The antibody can also be the antibody J28, a fragment or derivative thereof, or an antibody which essentially binds to the same epitope or determinant as the former. The composition can also comprise a pharmaceutically acceptable support. In a particular embodiment, said antibody is coupled with an antitumoral substance.

The invention further relates to the use of an antibody according to the invention or of a pharmaceutical composition comprising such antibody as medicament. In particular, the invention relates to the use of an antibody according to the invention or of a pharmaceutical composition comprising such antibody for preparing a medicament intended for the preventive or curative treatment of a pancreatic pathology, preferably pancreatic cancer, or breast cancer. Preferably, the antibody is the antibody 16D10, a fragment or derivative thereof, or an antibody which essentially binds to the same epitope or determinant as the former. The antibody can also be the antibody J28, a fragment or derivative thereof, or an antibody which essentially binds to the same epitope or determinant as the former. In a particular embodiment, said antibody is coupled with an antitumoral substance.

The invention relates to a method of preventive or curative treatment of a subject suffering from a pancreatic pathology, in particular pancreatic cancer, or breast cancer, comprising administering to said subject an effective amount of an antibody according to the invention, said administration resulting in a decrease or disappearance of the pancreatic pathology, in particular pancreatic cancer, or breast cancer, in the subject. Preferably, the antibody is the antibody 16D10, a fragment or derivative thereof, or an antibody which essentially binds to the same epitope or determinant as the former. The antibody can also be the antibody J28, a fragment or derivative thereof, or an antibody which essentially binds to the same epitope or determinant as the former. In a particular embodiment, said antibody is coupled with an antitumoral substance.

In another protocol the usual dose, which varies according to the subject being treated and the causal disease, can be for example from 1 to 10 mg of the monoclonal antibody described in example 18 hereinbelow per kilogram of body weight administered systemically in humans, once a week for two weeks.

The invention is also directed at providing new products (glycopeptides, antibodies, etc.) as well as other better, more effective or purer products than those described in the prior art.

The invention is illustrated in the following examples.

LEGENDS OF FIGURES

FIG. 1. Study comparing the reactivity of mAbJ28 and ma16D10 in two pancreatic tumor tissues (PDAC=ADK1 and PDAC4=ADK4).

Figure 2:
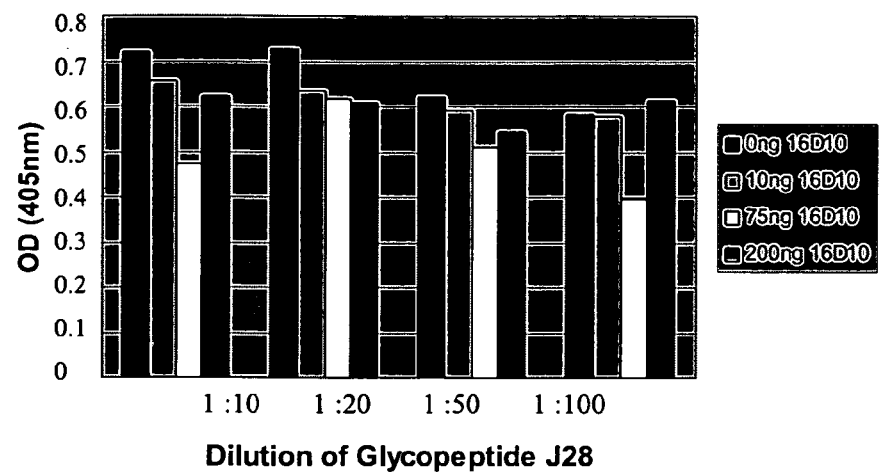
Figure 2:
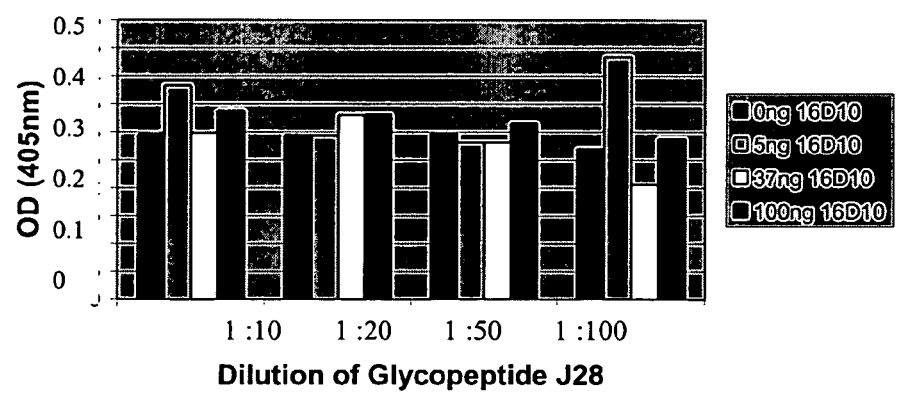

FIG. 2. Competition test between antibodies mAbJ28 and mAb16D10 for glycopeptide J28.

Figure 3:
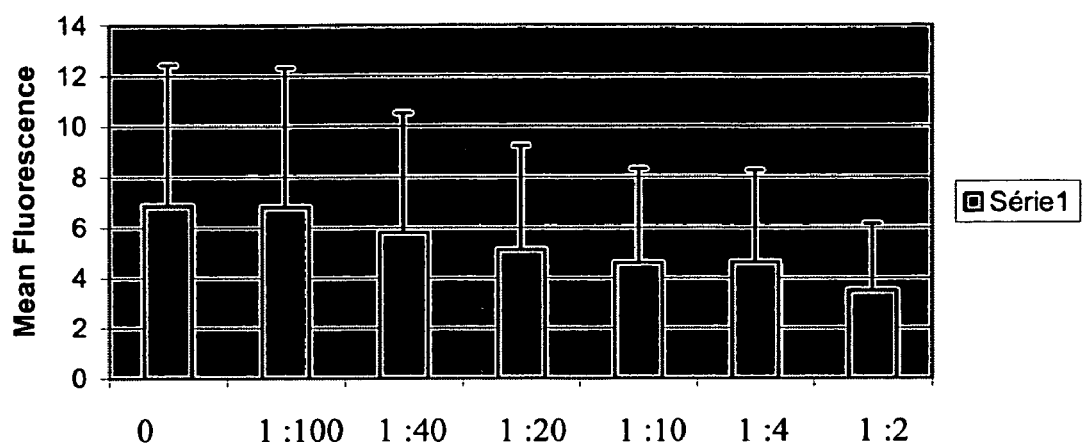

FIG. 3. Competition test between antibodies mAbJ28 and mAb16D10 in SOJ-6 cells.

Figure 4:
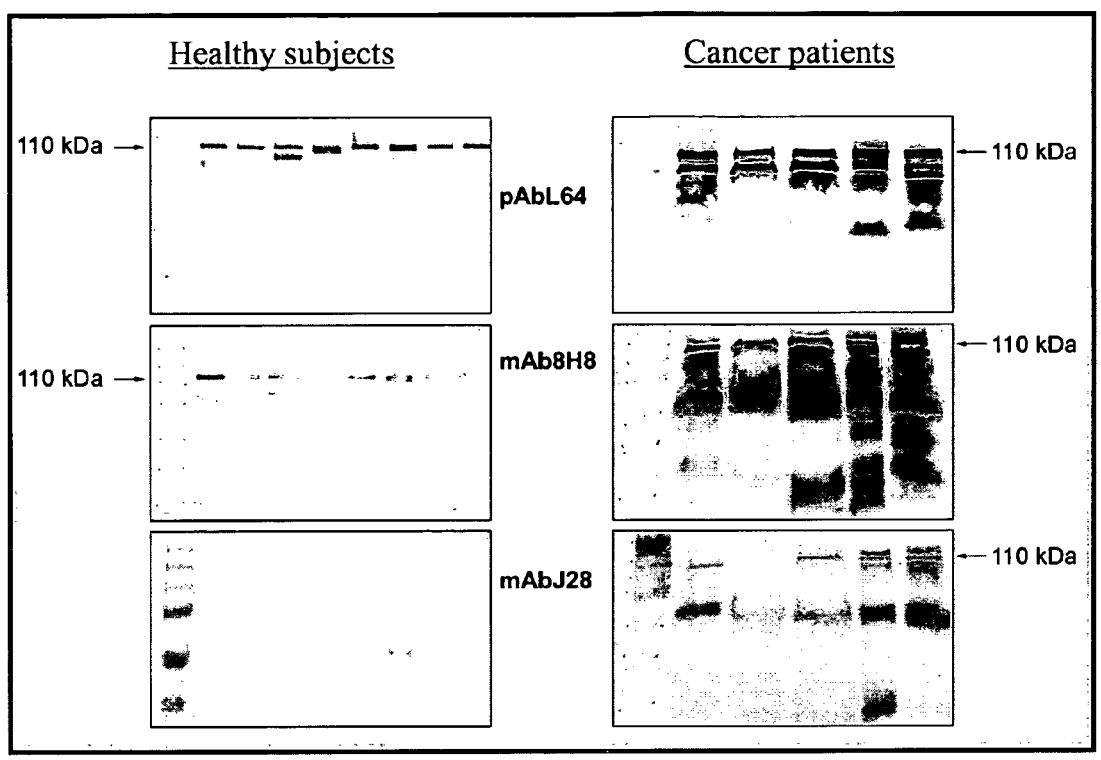

FIG. 4. Comparative immunodetection analysis in urine from healthy subjects (samples 29 to 36) and subjects with pancreatic cancer (samples 1 to 5) with the aid of polyclonal antibody pAbL64, monoclonal antibody mAb8H8 and monoclonal antibody mAbJ28. Urine proteins were separated on a 10% polyacrylamide gel then electrotransferred to a nitrocellulose membrane. The membranes were incubated with pAbL64, mAb8H8 or mAbJ28. The left lanes (Std) correspond to the molecular weight markers.

EXAMPLES

Preparation of Recombinant Glycopeptides

Recombinant glycopeptides of BSDL (SEQ ID No 9) and FAPP (SEQ ID No 13), were expressed in different strains derived from the well-known cell line CHO-K1, a Chinese hamster ovarian tumor cell line with fibroblast morphology, which can be obtained in particular from the *American Type Culture Collection* ATCC under the number CRL61 (Buck et al., 1958, J. Exp. Med., 108: 945-955).

The CHO-K1 cell line was chosen because it does not show detectable C2GnT glycosyltransferase, α(1-2)fucosyltransferase, α(1-3) fucosyltransferase, α(1-4) fucosyltransferase or α(1-3)galactosyltransferase activity in standard assay conditions.

Preparation of Plasmids (Cloned cDNA)

The cloned cDNAs enabling the expression of the different glycopeptide components were obtained by reverse transcription, carried out with a polydT polynucleotide probe (18 bases) hybridizing with the polyA tail of messenger RNA extracted from tissue samples of healthy human pancreas or the human pancreatic tumor cell line such as for example the cell line SOJ-6 [Fujii et al., 1990, Hum. Cell., 3: 31-36] originating from a human pancreatic adenocarcinoma, according to the method described by Chirgwin et al. [1979, Biochemistry, 18: 5294-5299].

Preparation 1

Plasmid pSec-FAPP

The amplification of cDNA coding for fetoacinar pancreatic protein (FAPP) (SEQ ID No 10) was reverse transcribed from 5 µg of total RNA extracted from the human pancreatic tumor line SOJ-6 mentioned earlier (45 minutes at 55° C., reverse transcription kit, Sigma, St Louis, Mo., USA) and followed by a PCR using the nucleotide primers C-ter/FAPP-BSDL and N-ter/FAPP, defined from the cDNA sequence coding for human BSDL (SEQ ID No 6) in the conditions described hereinbelow. The polymerase chain reaction was carried out with an "Advantage-GC cDNA PCR" kit (Clontech) enabling amplification of nucleotide sequences particularly rich in guanine and cytosine. The following program was employed: one cycle of 2 minutes at 94° C. followed by 35 cycles of 1 minute at 94° C. (denaturation), 1 minute at 52° C. (primer annealing), and 4 minutes at 68° C. (extension), followed by one cycle of 10 minutes at 68° C., in a Robocycler Gradient 96 thermocycler (Stratagene).

The primers had the following sequences:

```
N-ter/FAPP (SEQ ID No 1):
5'-TTCGTaagcttGCGAAGCTGGGCGCCGTGTACAGAA-3';

C-ter/FAPP-BSDL (SEQ ID No 2):
5'-TTTCGTgaattcACGCTAAAACCTAATGACTGCAGGCATCTG-3'.
```

The C-ter/FAPP-BSDL primer (SEQ ID No 2) which was used comprises a termination codon so as to eliminate translation of the c-myc epitope as well as that of the 6x-histidine tag carried by the commercial vector.

The cDNA (nucleotides 1 to 2169) amplified in this manner (SEQ ID No 12) does not comprise a signal peptide.

The resulting cDNA was then cloned into plasmid pSec-Tag (Invitrogen, Leek, the Netherlands).

Preparation 2

Plasmid pSec-16R

The cDNA coding for the C-terminal part of BSDL (from nucleotide 1089 Phe364 to nucleotide 2169: stop codon; SEQ ID Nos 8 and 9) from RNA extracted from normal pancreas was amplified by PCR using the primers C-ter/FAPP-BSDL (primer SEQ ID No 2, see Preparation 1) and N-ter-Ct.

The N-ter-Ct primer had the following sequence:

```
N-ter-Ct (SEQ ID No 3):
5'-CGTCTAaagcttTTTGATGTCTACACCGAGTCC-3'.
```

The polymerase chain reaction was carried out in the conditions described earlier (see Preparation 1).

The resulting cDNA was then cloned into plasmid pSec-Tag.

Preparation 3

Plasmid pSec-6R

The cDNA coding for the C-terminal part of FAPP (from nucleotide 1089: Phe364 to nucleotide 1839: stop codon; SEQ ID Nos 12 and 13) present in the plasmid pSec-FAPP was amplified by PCR using nucleotide primers No 2 (C-ter/FAPP-BSDL) and No 3 (N-ter-Ct) described hereinabove.

The polymerase chain reaction was carried out in the conditions described in preparation 1.

The resulting cDNA was then cloned into plasmid pSec-Tag.

Preparation 4

Plasmid pBK-αGT

The cDNA coding for α(1-3) galactosyltransferase (from nucleotide −10 to nucleotide +1122: stop codon) from RNA extracted from mouse heart (Balb/c mice) was amplified by PCR using the primers Cter/αGal and Nter/αGal defined from the cDNA sequence coding for mouse α(1-3) galactosyltransferase. These primers had the following sequence:

```
Nter/αGal (SEQ ID No 4):
5'-AAAAAgaattcGGAGAAAATAATGAAT-3'.

Cter/αGal (SEQ ID No 5):
5'-AAAAAgggcccACAAAGTCAGACATTAT-3'.
```

The polymerase chain reaction was carried out with the "Taq PCR Master Mix" kit (Qiagen, Courtaboeuf, France) according to the following program: one cycle of 2 minutes at 94° C. followed by 35 cycles of 1 minute at 94° C. (denaturation), 1 minute at 54° C. (primer annealing), and 2 minutes at 74° C. (extension), then one cycle of 10 minutes at 74° C., in a Gene Amp PCR System 2400 thermocycler (Perkin Elmer).

The resulting cDNA was then cloned into plasmid pBK-CMV (Stratagene, La Jolla, Calif., USA).

Preparation 5

Plasmid pcDNA3-C2β6GnT-flag

The cDNA coding for glycosyltransferase Core2 β(1-6) N-acetylglucosaminyltransferase described by Panicot et al. in Glycobiology, 1999, 9: 935-946 was cloned into the vector pcDNA-3 which at its 3' end comprises a sequence encoding the flag epitope. Expression of the flag epitope allows detection of C2GnT expression in the transformed cells.

The following steps were common to the plasmid preparations:

a) Ligation

The different PCR products were analyzed on a 1% agarose gel, purified using the "Geneclean" kit (Bio 101), then subcloned into the shuttle vector pCR2.1 TOPO and sequenced (Euro Sequences Genes Service, Paris, France) with the universal M13 and reverse M13 primers. The PCR products were then released from said shuttle vector by the action of the restriction enzymes HindIII and EcoRI and cloned into the eukaryote expression and secretion plasmid pSec-Tag to yield plasmids pSec-FAPP and pSec-16R (16R for C-terminal domain of BSDL) (SEQ ID No 8). The complementary DNA coding for the C-terminal part of FAPP, obtained by PCR, was directly cloned after purification and HindIII/EcoRI digestion into the pSec-Tag plasmid to yield plasmid pSec-6R (6R for C-terminal of domain FAPP) (SEQ ID No 12). Sequencing was carried out with the universal T7 primer and the BGH reverse primer synthesized for this purpose by Euro Sequences Gènes Service.

The PCR product coding for α(1-3) galactosyltransferase was released with the restriction enzymes EcoRI and ApaI, purified, then directly ligated into the EcoRI/ApaI sites of the vector pBK-CMV to yield plasmid pBK-αGT.

B) Bacterial Transformation

A 5 μl aliquot of the ligation product was contacted with 50 μl of competent bacterial cells (*Escherichia coli*, strain TOP10F') according to the protocol described by Hanahan [Hanahan, 1983, J. Mol. Biol., 166: 557-580]. Two microliters of 0.5 M β-mercaptoethanol were added and the sample was kept on ice for 30 minutes, then heat-shocked at 42° C. for 30 seconds, and immediately put back on ice. After 2 minutes, the sample was diluted in 450 μl of SOC medium (Life Technologies). The bacterial suspension was incubated for 1 hour at 37° C. with shaking. The bacteria were then spread, using glass beads, on Petri dishes containing Luria-Bertagni agar supplemented with 50 μg/ml ampicillin.

C) Plasmid Purification

The bacterial colonies which appeared after 18 hours of culture on selective agar medium (50 μg/ml ampicillin) were picked and inoculated in 2 ml of Luria-Bertagni liquid medium containing 50 μg/ml ampicillin. The cultures were incubated for 8 hours at 37° C. with shaking, then 1.5 ml of the bacterial suspension was centrifuged at 5,000 g for 5 minutes. The bacterial pellet was taken up in 100 μl of bacterial membrane destabilizing buffer (50 mM Tris-HCl pH 8, 10 mM EDTA, Ribonuclease A 100 μg/ml). The bacterial suspension was lysed by addition of 200 μl of alkaline lysis buffer (200 mM NaOH, 1% SDS) and the pH of the preparation was neutralized with 150 μl of 3 M potassium acetate pH 5.5. The alkaline lysis and neutralization steps require a 5-minute incubation on ice. Cell debris, denatured proteins and chromosomal DNA were eliminated by centrifugation at 10,000 g for 10 minutes at 4° C. The supernatant was then extracted with phenol-chloroform by 1:2 dilution in phenol/chloroform/isoamyl alcohol (25/24/1 V/V/V) stabilized to pH 8 with 100 mM Tris-HCl. The aqueous and organic phases were separated by centrifugation at 10,000 g for 2 minutes at room temperature. The upper aqueous phase was recovered and diluted 1:3 in absolute ethanol (−20° C.). Plasmid DNA was precipitated by centrifugation at 12,000 g for 15 minutes at 4° C., then washed twice with 70% ethanol. Plasmid DNA was then resuspended in 20 μl of ultra-pure water and stored at −20° C.

Preparation of Cell Clones

Preparation 6

Cell clone CHO-C2 and General Points Regarding the Obtaining of Intermediate Cell Clones A CHO-K1 cell line was transfected with plasmid pcDNA3-C2β6GnT-flag comprising the cDNA coding for the glycosyltransferase Core2 β(1-6) N-acetylglucosaminyltransferase (C2GnT), which at its 3' end comprises a sequence coding for the flag epitope. Expression of the flag epitope allows detection of C2GnT expression in the transformed cells.

To this effect, CHO-K1 cells were grown in HAM-F12 medium. When the cells reached 60 to 80% confluence, the culture medium was removed, the cell surface washed three times with Opti-MEM medium then covered with 200 μl of transfection solution diluted in Opti-MEM medium without fetal calf serum. The transfection solution contained the aforementioned plasmid and a lipofectamine liposome suspension (Life Technologies).

The cells were kept like this for 16 hours at which time the transfection supernatant was replaced with 2 ml of complete HAM-F12 medium containing a suitable selective antibiotic (neomycin, zeocin or hygromycin) for a period of at least four weeks. Clones resistant to the action of the antibiotic were isolated and then amplified.

The CHO-K1 cell clone selected in this manner with neomycin (250 μg/ml) was named CHO-C2.

Said clone CHO-C2 was then transfected with plasmid pSec-16R as described below for preparation 7. The clone resulting from transformation of CHO-C2 cells with plasmid pSEC-16R was selected with zeocin (1 mg/ml) and named CHO-C2-16R.

CHO-K1 cells were also cotransfected with plasmid pCDM7-FUT3 coding for fucosyltransferase 3 described by Kukowska-Lallo et al. (1990, Genes Dev. 4: 1288-1303), and plasmid pMamNeo according to the method described hereinabove. The CHO-F3 clone resulting from transformation of CHO-K1 cells with plasmid pCDM7-FUT3 was selected on the one hand with neomycin (250 μg/ml) and on the other hand for its high expression of sialyl Lewis x motifs. Said expression was detected by indirect immunofluorescence with the aid of the antibody CSLEX-1 (Becton-Dickinson). In this manner clone CHO-F3 was obtained.

Said clone CHO-F3 was then transfected with plasmid pSec-16R as described below for preparation 7. The clone resulting from transformation of CHO-F3 cells with plasmid pSec-16R and selection with zeocin (1 mg/ml) was named CHO-F3-16R.

CHO-K1 cells were also transfected with plasmid pCDM8-FUT7 coding for fucosyltransferase 7 described by Lowe et al. (1991, J. Biol. Chem. 266: 17467-17477) instead of plasmid pCDM7-FUT3, then with plasmid pSec16R. After selection with zeocin and neomycin in the conditions described earlier, the resulting clone was named CHO-F7-16R.

To prepare the intermediate clones expressing the C-terminal peptide of FAPP (6R), the aforementioned method was employed by transfecting the cell lines or cell clones CHO-K1, CHO-C2 and CHO-F3 with plasmid pSec-6R instead of plasmid pSec16R (see method described in preparation 7). However, only the glycosyltransferases C2GnT and fucosyltransferase 3 required to build the J28 glycosylated epitope were used during preparation of the cell lines.

Three intermediate cell clones CHO-6R, CHO-C2-6R and CHO-F3-6R were thus obtained after antibiotic selection in the conditions described hereinabove.

Preparation 7

Cell Clone CHO-16R

CHO-K1 cells were transfected with plasmid pSec-16R, which corresponds to plasmid pSec-Tag (Invitrogen, Leek, the Netherlands) into which the cDNA coding for the C-terminal domain of BSDL was cloned (see preparation 2). This was carried out as for the preparation of clone CHO-C2 in preparation 6.

The pSec-Tag plasmid carries a sequence coding for the V-J2C region of the mouse immunoglobulin κ light chain. Said sequence directs the protein encoded by the cDNA cloned in the plasmid to the secretory pathway of the eukaryotic cell in which it has been transfected.

The clone resulting from transformation of CHO-K1 cells with plasmid pSec-16R was named CHO-16R and was selected for expression of the corresponding (glyco)peptide [(glyco)peptide 16R].

Preparation 8

Cell Clone CHO-C2-F3-16R

Clone CHO-C2 from preparation 6 was transfected with plasmid pCDM7-FUT3 and with plasmid pLSVHg (R & D Systems) conferring hygromycin resistance, to yield cell clone CHO-C2-F3.

The CHO-C2-F3 cell line was transfected with plasmid pSec-16R as in preparation 7. The clone resulting from transformation of CHO-C2-F3 cells with plasmid pSec-16R was named CHO-C2-F3-16R.

CHO-C2-F3-16R expresses sialyl Lewis×motifs and shows reactivity towards antibody pAbL64.

Preparation 9

Cell Clone CHO-C2-F7-16R

This was obtained as in preparation 8, but by using plasmid pCDM8-FUT7 instead of plasmid pCDM7-FUT3.

The clone resulting from transformation of CHO-C2-F7 cells with plasmid pSec-16R was named CHO-C2-F7-16R and the corresponding cell line was deposited with the Collection Nationale de Culture de Microorganismes (CNCM), Institut Pasteur, 28, rue du Dr Roux, 75724 Paris Cédex 15, France on 16 Mar. 2004 under the number 1-3189.

The clones CHO-C2-F3-16R and CHO-C2-F7-16R from preparations 8 and 9 express sialyl Lewis x motifs and show reactivity towards antibody pAbL64.

Preparation 10

Cell Clone CHO-C2-F3-6R

Clone CHO-C2-F3 from preparation 8 was transfected with plasmid pSec-6R (see preparation 3) as described for preparations 6 and 7 to yield clone CHO-C2-F3-6R. This clone expresses a peptide bearing among others a glycosylated epitope recognized by monoclonal antibody J28.

Preparation 11: Cell Clone CHO-C2-F3-GT-6R

Clone CHO-C2-F3-6R from preparation 10 was transfected with plasmid pBK-αGT (see preparation 4) as described earlier to yield clone CHO-C2-F3-GT-6R bearing the glycosylated epitope recognized by monoclonal antibody J28 as well as the glycosylated epitope αGal recognized by natural circulating antibodies in human blood.

Example 1

Recombinant Glycopeptide Having the Size and the Characteristics of Those Corresponding to the C-Terminal End of BSDL (CHO-16R)

The recombinant glycopeptide was produced by routine culture of cell clone CHO-16R (preparation 7) for 16 hours at 37° C. in a humid, 5% $CO_2$ atmosphere in Opti-MEM medium (Invitrogen) containing 2 mM L-glutamine, 100 U/ml penicillin, 100 mg/ml streptomycin and 0.1% fongizone supplemented with suitable selective antibiotics. The cells were seeded at a density of $2 \times 10^4$ cells/cm$^2$.

The culture medium was changed every 48 hours. When the cells reached confluence, they were washed in phosphate buffer (PBS) without $CaCl_2$ and without $MgCl_2$, then detached with trypsin/0.05% EDTA, sedimented by low speed centrifugation (400 g for 3 min) and resuspended in 5 ml of culture medium.

Intracellular immunofluorescence and flow cytometry were used to check that the cell clones expressed the recombinant glycopeptide of interest.

The recombinant glycopeptide was purified by liquid chromatography followed by affinity chromatography and analyzed by SDS-PAGE.

It could be seen on the gel that the secreted peptide resolved into two different molecular weight bands of approximately 78 kDa and 83 kDa.

The 83 kDa band probably corresponds to the glycosylated peptide whereas the 78 kDa band would either be a non-glycosylated form or a form with less glycosylation.

It therefore appears that the aforementioned clone expressed a glycopeptide having the size and the characteristics of those corresponding to the C-terminal end of BSDL.

Example 2

Recombinant Glycopeptide Having the Size and the Characteristics of Those Corresponding to the C-Terminal End of BSDL (CHO-C2-16R)

The method described in example 1 was employed, but by culturing the cell clone CHO-C2-16R (preparation 6).

The recombinant glycopeptide obtained was purified by liquid chromatography followed by affinity chromatography and analyzed by SDS-PAGE.

It could be seen on the gel that the secreted peptide resolved into two different molecular weight bands of approximately 78 kDa and 83 kDa.

It therefore appears that the aforementioned clone expressed a glycopeptide having the size and the characteristics of those corresponding to the C-terminal end of BSDL.

Example 3

Recombinant Glycopeptide Having the Size and the Characteristics of Those Corresponding to the C-Terminal End of BSDL (CHO-F3-16R)

The method described in example 1 was employed, but by culturing the cell clone CHO-F3-16R (preparation 6).

The recombinant glycopeptide obtained was purified by liquid chromatography followed by affinity chromatography and analyzed by SDS-PAGE.

It could be seen on the gel that the secreted peptide resolved into two different molecular weight bands of approximately 78 kDa and 83 kDa.

It therefore appears that the aforementioned clone expressed a glycopeptide having the size and the characteristics of those corresponding to the C-terminal end of BSDL.

Example 4

Recombinant Glycopeptide Having the Size and the Characteristics of Those Corresponding to the C-Terminal End of BSDL (Cho-C2-F3-16R)

The method described in example 1 was employed, but by culturing the cell clone CHO-C2-F3-16R (preparation 8).

The recombinant glycopeptide obtained was purified by liquid chromatography followed by affinity chromatography and analyzed by SDS-PAGE.

It could be seen on the gel that the secreted peptide resolved into two different molecular weight bands of approximately 78 kDa and 83 kDa.

It therefore appears that the aforementioned clone expressed a glycopeptide having the size and the characteristics of those corresponding to the C-terminal end of BSDL.

Example 5

Recombinant Glycopeptide Having the Size and the Characteristics of Those Corresponding to the C-Terminal End of BSDL (Cho-F7-16R)

The method described in example 1 was employed, but by culturing the cell clone CHO-F7-16R (preparation 6).

The recombinant glycopeptide obtained was purified by liquid chromatography followed by affinity chromatography and analyzed by SDS-PAGE.

Only one band of molecular weight 83 kDa was seen on the gel.

Example 6

Recombinant Glycopeptide Having the Size and the Characteristics of Those Corresponding to the C-Terminal End of BSDL (CHO-C2-F7-16R)

The method described in example 1 was employed, but by culturing the cell clone CHO-C2-F7-16R (preparation 9).

The recombinant glycopeptide obtained was purified by liquid chromatography followed by affinity chromatography and analyzed by SDS-PAGE.

It could be seen on the gel that the secreted peptide resolved into two different molecular weight bands of approximately 78 kDa and 83 kDa.

It therefore appears that the aforementioned clone expressed a glycopeptide having the size and the characteristics of those corresponding to the C-terminal end of BSDL.

It therefore appears that all the aforementioned clones (16R) expressed glycopeptides having the size and the characteristics of those corresponding to the C-terminal end of BSDL.

Examples 7 to 13

Recombinant Glycopeptides Having the Size and the Characteristics of Those Corresponding to the C-Terminal End of FAPP The recombinant polypeptides produced by clones CHO-K1 (control), CHO-6R (Ex 7), CHO-C2-6R (Ex 8), CHO-F3-6R (Ex 9), CHO-C2-F3-6R (Ex 10), CHO-GT-6R (Ex 11), CHO-C2-GT-6R (Ex 12) and CHO-C2-F3-GT-6R (Ex 13), were purified on a polyacrylamide gel or else by liquid and/or affinity chromatography and analyzed by immunodetection using antibody pAbL64 described by Abouakil et al., 1988, Biochim. Biophys. Acta, 961: 299-308, and mAbJ28. The mouse monoclonal antibody mAbJ28, specific of the fucosylated J28 glycopeptide derived from O-glycosylation of the oncofetal form of FAPP, is described by Panicot et al. in Glycobiology, 1999, 9: 935-946.

The anti-BSDL polyclonal antibody pAbL64 was obtained by immunizing rabbits after purifying the antigen from human pancreatic juices. Said antibody perfectly recognizes FAPP, the oncofetal form of BSDL.

The polyclonal antibody specific of the BSDL protein core, named antipeptide, was obtained by immunizing rabbits with a synthetic peptide corresponding to the peptide sequence of BSDL comprised between the serine residue in position 346 and glutamine in position 370 coupled to hemocyanin.

Said two antibodies were purified on a protein A-Sepharose 4B column (Pharmacia). The antipeptide was subjected to a second purification step by affinity chromatography on a column of keyhole limpet hemocyanin (KLH) coupled to Sepharose gel to eliminate anti-KLH antibodies.

The recombinant peptides produced by the different clones of the 6R type were loaded at 100 µg per lane on a 10% polyacrylamide gel, separated, then electrotransferred to a nitrocellulose membrane. The membranes were then incubated in the presence of antibody pAbL64 on the one hand, and antibody mAbJ28 on the other hand, and developed.

In both cases, the antibodies employed bound specifically to polypeptides having a size of 50 kDa, corresponding to the expected size of the C-terminal glycopeptides of FAPP, except in the case of the non-transfected CHO-K1 cell line used as negative control.

Examples 14 to 19

Anti-Glycopeptide Monoclonal Antibodies

Recombinant anti-glycopeptide antibodies having the size and the characteristics of those corresponding to the C-terminal end of FAPP were prepared as follows:

Stage A—Immunization of Mice.

Six-week-old male Balb/c mice were immunized according to the following protocol:

Day 0: Intraperitoneal injection of 25 µg of a mixture of FAPP and BSDL purified from normal and pathological human pancreatic juices (hereinbelow named BSDL-FAPP antigen) in a 50:50 emulsion (150 µl NaCl/150 µl complete Freund's adjuvant).

Day 15: Intraperitoneal challenge with 25 µg of BSDL-FAPP antigen in a 50:50 emulsion (150 µl NaCl/50 µl incomplete Freund's adjuvant).

Day 30: Intraperitoneal challenge with 25 µg of BSDL-FAPP antigen in a 50:50 emulsion (150 µl NaCl/150 µl incomplete Freund's adjuvant).

Day 110: Intraperitoneal challenge with 20 µg of BSDL-FAPP antigen in a 50:50 emulsion (150 µl NaCl/150 µl incomplete Freund's adjuvant).

Day 140: Intraperitoneal challenge with 20 µg of BSDL-FAPP antigen in a 50:50 emulsion (150 µl NaCl/150 µl incomplete Freund's adjuvant).

Day 215: Intraperitoneal challenge with 20 µg of BSDL-FAPP antigen in a 50:50 emulsion (150 µl NaCl/150 µl incomplete Freund's adjuvant).

Day 244: Intravenous injection of 10 µg of BSDL-FAPP antigen in 100 µl of sterile NaCl.

Day 247: Cell fusion.

Stage B—Cell Fusion According to the Protocol of Köhler and Milstein.

a) At day 247, the selected mouse was sacrificed and the spleen removed and ground up. The spleen cells were washed in RPMI 1640 medium. P3.X63.Ag8 653 myeloma cells, previously grown in RPMI 1640 medium containing 20% fetal calf serum (FCS), 1% glutamine, 1% nonessential amino acids and 1% sodium pyruvate were also washed in the same medium.

At the same time, peritoneal macrophages were collected by peritoneal lavage of non-immunized Balb/c mice with RPMI.

For hybridoma formation, the spleen cells and myeloma cells were mixed in a tube at a ratio of 5 spleen cells for 1 myeloma cell. After centrifugation, the cell pellet was resuspended in 800 µl of 50% polyethylene glycol 1500 in 75 mM Hepes buffer pH 7.5. After 1 minute of contact at 37° C., 20 ml of RPMI 1640 medium were slowly added to the fused cells.

b) The initial culture was carried out on 96-well microtitration plates in the presence of RPMI medium containing 20% fetal calf serum (FCS) and supplemented with $5 \times 10^{-3}$ M hypoxanthine, $2 \times 10^{-5}$ M aminopterin and $8 \times 10^{-4}$ M thymidine. Next, $5 \times 10^3$ peritoneal macrophages followed by $10^5$ fused cells were deposited in each well.

Stage C—Cloning and Subcloning.

Each hybridoma selected by the method described in stage D hereinbelow resulted from cloning by a limit dilution technique in which 10, 5, 2, 1 and 0.5 cells were statistically distributed into microwells containing peritoneal macrophages. Two subclonings were thus carried out, each clone and subclone having been replicated then frozen in 90% FCS and 10% dimethylsulfoxide (DMSO). Subclones from the last generation were then expanded in vivo to obtain ascites fluid in the Balb/c mice, followed by immunoglobulin purification on a protein A column.

Stage D—Hybrid Cell Selection Method.

Selection was carried out by a liquid phase ELISA method using culture supernatant. Five micrograms of BSDL-FAPP antigen in 100 µl of bicarbonate buffer pH 8.5 were deposited in the wells of a 96-well ELISA plate. The plate was activated for 12 h at 4° C. and saturated for 2 hours with 300 µl of 1 mg/ml bovine albumin. The plates were then washed and incubated with 100 µl of cell culture supernatants potentially containing antibodies directed against the BSDL-FAPP antigen. After a 2-hour incubation, the plates were washed and incubated for 2 hours with alkaline phosphatase-labelled secondary antibodies. At the end of the incubation, the plates were again washed and incubated with para-nitrophenylphosphate (100 µl, 1 mg/ml in 0.2 M Tris/HCl buffer pH 8.2 and 1 mM $CaCl_2$). After 1 hour at 37° C., the plates were read on a microplate reader at 410 nm.

About 15 antibodies were selected for their response in the ELISA test. Additional analyses by Western blot (immunoimprinting) using FAPP as immunogenic protein enabled the selection of hybridomas 7B4 (Example 14), 11D7 (Example 15), 14H9 (Example 16), 14H10 (Example 17), 16D10 (Example 18) and 8H8 (Example 19).

Cells producing the IgM antibody 16D10 were deposited with the Collection Nationale de Culture de Microorganismes (CNCM), Institut Pasteur, 28, rue du Dr Roux, 75724 Paris Cédex 15, France on 16 Mar. 2004 under the number I-3188.

Example 20

Preparation of Membrane Glycopeptides of Natural Origin

Membrane glycopeptides carrying epitopes recognized by the monoclonal antibodies described in examples 14 to 19 were prepared in the following manner pancreatic tumor cells were cultivated on a plastic support then detached therefrom with non-enzymatic dissociation solution (Sigma). The cell pellet obtained by centrifugation (2 min at 1000 rpm) was sonicated (2×15 sec) and again centrifuged (20 min, 14,000 rpm, 4° C.). The pellet suspended in phosphate buffer corresponds to membrane glycopeptides carrying epitopes recognized by the monoclonal antibodies described in examples 14 to 19.

Example 21

A vaccine having the following composition was prepared

| | |
|---|---|
| membrane glycopeptides from example 20 isolated from HaPT-1 pancreatic cells, | 20 µg |
| ALU-gel-ser adjuvant (Serva) | 150 µl |
| excipient including water for injections | 150 µl |

Vaccination was carried out by intraperitoneal injection two weeks then one week before transplanting the tumor cells into the flank of the animals. The result of said vaccination was compared to that of a placebo (injection of isotonic solution).

Example 22

A 0.5 mg/ml injectable isotonic solution of antibodies from example 18 (16D10) was prepared.

Control Example 1

Recombinant Glycopeptide Having the Size and the Characteristics of Those Corresponding to the C-Terminal End of BSDL The method described in example 1 was employed, but by cultivating the cell clone CHO-K1.

The gel did not show any bands at molecular weight 78 kDa or 83 kDa.

Pharmacological Study

Experiment 1

Use of Recombinant C-Terminal Glycopeptides of BSDL and FAPP in Cellular Immunotherapy of Exocrine Pancreatic Cancer Operating Protocol:

Hamsters (90-100 g) were divided into several groups and vaccinated with HaPT-1 cells inactivated by 30 minutes of UV exposure. The hamsters were inoculated with the glycopeptides from example 20 and inactivated cells mixed with ALU-gel-ser adjuvant by intraperitoneal injection once a week for two weeks. Two weeks after the last inoculation, the hamsters received an ectotopic transplantation of HaPT-1 cells (subcutaneous, on the flank).

Tumor growth was monitored weekly and tumor volume was compared with the control group vaccinated with a placebo (PBS alone).

Results:

The tumor growth curve was significantly slower in hamsters immunized with the glycopeptides from example 20 (antigens represented in large part by structures recognized by monoclonal antibodies J28 and 16D10 (Example 18), directed against the C-terminal domain of BSDL and/or FAPP).

At the end of the experiment, tumor volume in the group vaccinated with inactivated cells was 80% lower than in the control group.

The hamsters were sacrificed and pancreatic and tumor tissue samples were removed for immunohistochemical analysis. Monoclonal antibodies J28 and 16D10 and polyclonal antibody L64 were used to test for expression of the 16D10 and J28 epitopes (recognized by monoclonal antibodies J28 and 16D10, respectively) and the FAPP protein core.

Examination of the tumor tissue slices revealed a decrease in the expression of the 16D10 and J28 epitopes (smaller decrease for the latter), between the group vaccinated with inactivated cells and the control group.

Therefore, the C-terminal glycopeptides of BSDL and FAPP according to the invention can be used in cellular immunotherapy of exocrine pancreatic cancer.

Experiment 2

Use of the Glycopeptides According to the Invention in the Diagnosis of Diabetic Pathologies Operating Protocol:

A series of experiments carried out by the ELISA method on sera from patients suffering from various pancreatic and other pathologies showed that BSDL, used as antigen to activate the ELISA plates, was specifically recognized by antibodies present in approximately 80% of the sera from patients with type I diabetes whereas less than 10% of the sera from control patients were reactive. Sera from patients with other pathologies such as pancreatitis, pancreatic cancer or Graves' disease were not reactive (Panicot et al. 1999, Diabetes, 48: 2316-2323).

The recombinant glycopeptides from examples 2, 5 and 6 were tested by Western blot (or immuno-imprinting).

Results:

BSDL, and in particular the C-terminal domain thereof, was recognized by sera from diabetic patients whereas BSDL was not recognized by sera from normal control patients.

The recombinant glycopeptides from examples 2 and 6 were recognized by sera from diabetic (type I) patients.

The control sera (from healthy patients) did not recognize any of said three glycopeptides.

Therefore, the natural and recombinant C-terminal glycopeptides of the invention described in the examples can be used for the diagnosis of diabetic pathologies.

Experiment 3

Use of Monoclonal Antibodies Directed Against the C-Terminal Domain of FAPP and/or BSDL in the Diagnosis of Pancreatic Cancer Operating Protocol:

Human pancreatic tumor cell lines SOJ-6 and Bx-PC-3 and human non-pancreatic tumor cell lines Caco-2 and Hep-G2 were treated with monoclonal antibodies J28, 16D10 (Example 18), and 8H8 (Example 19) and with polyclonal antibody (pAb) L64 specific of the C-terminal domain of BSDL and FAPP. The respective antigen-antibody complexes were detected with the aid of a fluorescent rabbit or mouse fluorescein conjugated N-isothiocyanate anti-IgG antibody. FACS analysis was used to detect the presence of antigens associated with the C-terminal domain of FAPP and BSDL at their surface.

Results:

The monoclonal antibodies J28 and 16D10 (Example 18), and the polyclonal antibody (pAb) L64 specifically recognized the surface of the human pancreatic tumor cell lines SOJ-6 and Bx-PC-3 and did not recognize the surface of the human non-pancreatic tumor cell lines which were tested, such as Caco-2 and Hep-G2 cells.

The monoclonal antibodies J28 and 16D10 directed against the glycosylated epitopes expressed specifically on the C-terminal domain of FAPP and BSDL are therefore capable of distinguishing pancreatic tumor cells from non-pancreatic tumor cells.

Therefore, the monoclonal antibodies directed against the glycosylated epitopes expressed specifically on the C-terminal domain of FAPP and BSDL can be used in the diagnosis of pancreatic cancer.

In particular said antibodies can determine whether a secondary tumor site (metastasis) is of pancreatic origin or from a primary tumor of another origin.

Experiment 4

Targeting of Pancreatic Neoplastic Cells by the Monoclonal Antibodies of the Invention A—Study on Human Pancreatic Tissue Sections.

Operating Protocol:

Tissue expression of the glycosylated epitopes recognized by the monoclonal antibodies directed against the C-terminal domain of FAPP and/or BSDL was tested in immunohistochemical studies carried out with the various monoclonal antibodies of the invention on normal and cancerous human pancreatic tissue sections.

In a first step, pancreatic tissue was obtained from four patients with pancreatic cancer and from five normal pancreas. The tissue sections were incubated with the antibodies from examples 18 (16D10) and 19 (8H8).

In a second step, seven human pancreatic tumor tissue samples and five non-tumoral tissues (diagnosed by a pathologist) were sliced into 5-μm thick sections, dried in acetone at 4° C. and rehydrated in Tris/HCl buffer pH 7.6. The sections were then incubated either for 1 h at 25° C. (mAbJ28 and mAb8H8, example 19) or overnight at 4° C. (mAb16D10, example 18), the antibodies being diluted 1:50 in Dako diluent (EnVision System, Dako, Copenhagen, Denmark). The sections were then incubated with a suitable alkaline phosphatase-labelled secondary antibody. The antigen-antibody complex was then detected with the chromogenic substrate Fast-Red. In the case of quantitative analysis by confocal laser scanning microscopy, the suitable secondary antibody was labelled with streptavidin-fluoroscein. The sections were then examined under a microscope or with a confocal laser fluorescence microscope.

Results:

In the first experiment, the monoclonal antibody from example 18 (16D10) specifically recognized neoplastic cells from four pancreatic tumor tissue samples.

No reaction was observed with the five normal pancreatic tissues.

The monoclonal antibody from example 19 (8H8) preferentially recognized normal pancreatic tissue.

In the second experiment, out of all seven tumor tissue samples studied, seven were recognized by mAb16D10 (example 18) and five by mAbJ28. The immunohistochemical results are presented in FIG. 1 and Tables 1 and 2. The mAb16D10 (example 18) showed very high specificity for tumor tissue whereas mAb8H8 (example 19) only recognized normal pancreatic tissue. mAbJ28 showed intermediate specificity since it preferentially recognized tumor tissue, but also some normal tissue. Table 2 presents the confocal laser microscopy results defining the fluorescence intensity on the antibody-labelled tissue sections. It should be noted that none of these antibodies recognized the other tumor tissues tested: liver, lung, stomach, colon, esophagus and thyroid.

The monoclonal antibodies of the invention coupled to an antitumoral active substance can be used in the treatment of pancreatic cancer to target and destroy pancreatic tumor cells.

Similarly, radioactive (or other) elements can be coupled to said antibodies and enable a precise localization of primary tumors and metastases. Said antibodies can also afford a clear and sharp differentiation between normal tissue and tumor tissue.

TABLE 1

Semi-quantitative immunohistochemical studies: results obtained with antibodies mAb8H8, mAbJ28 and mAb16D10

| | Label | | |
|---|---|---|---|
| | mAb8H8 | mAbJ28 | mAb16D10 |
| Control 1 | | | |
| Acini | 4 | 1 | 0 |
| Canals | 0 | 0 | 0 |
| Control 2 | | | |
| Acini | 4 | 1 | 0 |
| Canals | 0 | 0 | 0 |
| Control 3 | | | |
| Acini | 4 | 1 | 0 |
| Canals | 0 | 0 | 0 |
| Control 4 | | | |
| Acini | 4 | 1 | 0 |
| Canals | 0 | 0 | 0 |
| Control 5 | | | |
| Acini | 4 | 1 | 0 |
| Canals | 0 | 0 | 0 |
| PDAC1 | 0 | 0 | 4 |
| PDAC2 | 0 | 3 | 4 |
| PDAC3 | 0 | 2 | 4 |
| PDAC4 | 0 | 0 | 4 |
| PDAC5 | 1 | 3 | 4 |
| PDAC6 | 0 | 2 | 4 |

TABLE 1-continued

Semi-quantitative immunohistochemical studies: results obtained with antibodies mAb8H8, mAbJ28 and mAb16D10

| | Label | | |
|---|---|---|---|
| | mAb8H8 | mAbJ28 | mAb16D10 |
| PDAC7* | 0 | 1 | 3 |
| CCA* | 0 | 0 | 0 |
| ECA* | 0 | 0 | 0 |
| LiCa* | 0 | 0 | 0 |
| LuCa | 0 | 0 | 0 |
| SCA* | 0 | 0 | 0 |
| TCA* | 0 | 0 | 0 |

C, control;
PDAC, pancreatic adenocarcinoma;
LuCA, lung carcinoma;
CCA, colon carcinoma;
ECA, esophageal carcinoma;
LiCa, liver carcinoma;
SCA, stomach carcinoma;
TCA, thyroid carcinoma.
Tissues were obtained from the BioChain Institute (USA). The number of labelled cells is expressed semi-quantitatively as follows:
0, no labelling;
1: from 1 to 10% of cells were labelled;
2: from 10 to 30% of cells were labelled;
3: from 30 to 40% of cells were labelled and
4: >40% of cells were labelled.

TABLE 2

Fluorescence intensity on sections labelled with the antibodies of the invention.

| | Fluorescence intensity | | |
|---|---|---|---|
| Case | mAb8H8 | mAbJ28 | mAb16D10 |
| Control 1 | 92.33 ± 2.80 | 19.11 ± 8.75 | 31.41 ± 1.19 |
| Control 2 | 138.72 ± 3.36 | 14.54 ± 6.57 | 8.16 ± 5.16 |
| Control 3 | 110.95 ± 2.71 | 17.41 ± 8.09 | 0 |
| Control 4 | 109.04 ± 4.58 | 26.49 ± 12.01 | 0 |
| Control 5 | 114.14 ± 1.26 | 35.56 ± 16.30 | 0 |
| PDAC1 | 0 | 53.12 ± 2.12 | 124.02 ± 2.43 |
| PDAC 2 | 36.47 ± 0.35 | 87.88 ± 4.28 | 129.84 ± 6.35 |
| PDAC 3 | 0 | 89.60 ± 2.84 | 123.27 ± 6.16 |
| PDAC 4 | 17.06 ± 7.64 | 50.61 ± 2.36 | 143.95 ± 2.71 |
| PDAC 5 | 40.42 ± 0.22 | 88.92 ± 5.48 | 135.06 ± 4.03 |
| PDAC 6 | 0 | 59.97 ± 1.64 | 129.30 ± 1.91 |
| PDAC 7* | 18.65 ± 8.38 | 72.74 ± 4.84 | 132.34 ± 2.75 |

C, control;
PDAC, pancreatic adenocarcinoma.
Tissues were obtained from the BioChain Institute (USA). In each case the mean ± standard error of labelling on six different regions of each tissue slice are shown. Significant differences were observed between control and pancreatic tumor tissue for mAb16D10 ($P < 0.001$), mAb8H8 ($P < 0.001$) and mAbJ28 ($P < 0.05$).

B—ELISA Competition Studies Between mAbJ28 and mAb16D10 (Example 18) on the Recombinant Glycopeptide Carrying the J28 Glycotope.

Operating Protocol:

The glycosyltransferases involved in formation of the oncofetal glycotype J28 were characterized and said glycotope was reproduced ex vivo by genetic engineering. It was reconstructed in CHO cells from the recombinant C-terminal peptide of FAPP (composed of 6 repeated sequences) and two glycosyltransferases, α(1-3/4) fucosyltransferase FUT3 and Core 2 β(1-6) N-acetylglucosaminyltransferase required to build said structure. The recombinant C-terminal glycopeptide of FAPP carrying the J28 glycotype (example 10) was secreted in the culture supernatant of this cell line.

Competition experiments were carried out with an ELISA test in the presence of culture supernatant containing the recombinant C-terminal glycopeptide of FAPP carrying the J28 glycotype (example 10), biotinylated mAbJ28 and increasing concentrations of mAb16D10 (example 18) as competitor with the aim of demonstrating the specificity of said antibodies.

The principle of the protocol was as follows:

1. The bottom of the wells was coated with concentrated culture supernatant containing the recombinant J28 glycopeptide diluted 1:10, 1:20, 1:50, 1:100.

2. Biotinylated mAbJ28 was added at 10 ng per well (Exp. 1) or 5 ng per well (Exp. 2) together with increasing concentrations of purified mAb16D10.

3. Biotinylated mAbJ28 was recognized with the aid of an alkaline phosphatase-conjugated anti-biotin antibody (anti-biotin Ab control on mAb16D10=0).

Results:

FIG. 2 presenting the results of two experiments shows that there was no significant loss in the reactivity of mAbJ28 for its glycotope coated at the bottom of the wells in the presence of increasing concentrations of mAb16D10 (example 18) used as competitor (even with a four-fold excess).

C—FACS Competition Study Between Antibodies mAbJ28 and mAb16D10 on Human Pancreatic Tumor Cell Line SOJ-6.

Operating Protocol:

The monoclonal antibodies mAbJ28 and mAb16D10 specifically recognized human pancreatic tumor cell lines SOJ-6, Bx-PC-3 and did not recognize the human non-pancreatic tumor cell lines tested.

Preliminary competition experiments by FACS were carried out on the human pancreatic tumor cell line SOJ-6 in the presence of monoclonal antibody mAbJ28 coupled to a fluorochrome (Alexa 488) and increasing concentrations of monoclonal antibody mAb16D10 (example 18) used as competitor in the form of ascites fluid.

The principal of the protocol was as follows:

1. Human pancreatic tumor SOJ-6 cells were detached, fixed and saturated with BSA at 4° C.

2. Fluorescent-labelled monoclonal antibody mAbJ28 was added at 2 ng per sample in the presence of increasing concentrations of ascites fluid containing mAb16D10 at 1:100, 1:40, 1:20, 1:20, 1:10, 1:4 and 1:2 dilution.

3—The cells were analyzed by FACS.

Results:

The results are shown in FIG. 3. Despite a very low labelling of the cells (due to the first experiments with Alexa-488-labelled mAbJ28), no significant loss of reactivity of antibody mAbJ28 for its glycotype was observed in the presence of increasing concentrations of antibody mAb16D10 used as competitor.

Experiment 5

Use of the Monoclonal Antibodies of the Invention in the Treatment of Exocrine Pancreatic Cancer Experimental Protocol:

Two groups of six-week-old nude mice (NMRI mice) received an intraperitoneal inoculation on Day −1 either with monoclonal antibody 16D10 from example 18 at a dose of 150 µl of a 0.5 mg/mg isotonic antibody solution or with an isotonic placebo solution.

At Day 0, 2×10⁶ SOJ-6 human pancreatic tumor cells were subcutaneously injected into the right flank. The animals were then inoculated with monoclonal antibody 16D10 or isotonic solution at Days +1, +3, +6, +8 and +10 (in the quantities indicated hereinabove).

The volume of the palpable subcutaneous tumors was measured in each animal at weeks 1, 2, 3, 4, 5, 6, 7, 8, 9 and 10.

Results

The tumor growth rate in animals treated with the monoclonal antibody from example 18 was 10 times lower than that of placebo-treated animals.

At the end of the experiment (10 weeks post-inoculation), the median volume of tumors removed from control animals was 1.25 versus a markedly lower median value of 0.15 cm³ in the treated animals.

The monoclonal antibodies directed against the C-terminal domain of FAPP and/or BSDL and in particular the monoclonal antibody from example 18 can therefore be used in therapy for pancreatic cancer.

Experiment 6

Use of the Monoclonal Antibodies Directed Against the C-Terminal Domain of FAPP and/or BSDL in the Urinary Diagnosis of Pancreatic Cancer Operating Protocol:

A series of experiments carried out by Western blot, liquid chromatography and mass spectrometric characterization led to the identification of intact BSDL in the urine of healthy patients. In light of these findings, the different glycosylated epitopes J28, 16D10 carried by the C-terminal domain of BSDL/FAPP and which appear in pancreatic adenocarcinoma, might also be present in the urine of patients suffering from this cancer.

Results

FIG. 4 showing the initial results obtained in a preliminary Western blot experiment reveals the presence of the glycosylated J28 epitope carried by BSDL/FAPP in urine samples from patients with pancreatic adenocarcinoma, and the absence thereof in urine samples from healthy individuals.

FIG. 4 shows that both healthy subjects and cancer patients had one or two bands displaying immunoreactivity towards pAbL64 and mAb8H8 (example 19) located at 110 kDa. On the other hand, the two groups displayed different reactivity towards mAbJ28, a mAbJ28-immunoreactive band at 110 kDa being seen in cancer patients but not in healthy subjects.

Experiment 7

Use of Urinary C-Terminal Glycopeptides of BSDL and FAPP in Cellular Immunotherapy of Exocrine Pancreatic Cancer Operating Protocol:

Preliminary results showed that the glycosylated J28 epitope carried by BSDL/FAPP was present in urine samples from patients with pancreatic adenocarcinoma tested at the present time whereas it was absent in urine samples from healthy individuals. The presence of said tumor marker in urine, which can be obtained in large quantities without the use of invasive methods, can serve as a source of antigen in order to develop different active immunotherapy protocols such as described by Ramanathan et al., Cancer Immunol Immunoth, 2004, 54: 254-64; O'Neill et al., Blood, 2004, 104: 2235-46; Vlad et al., J Exp Med, 2002, 196: 1435-46; Schmidt et al., Cancer Res, 2003, 63: 8962-67. One such avenue is to develop autologous cell immunotherapy protocols (as described by Yamanaka et al., Br J Cancer, 2003, 89: 1172-9; Svane et al., Cancer Immunol Immunother, 2004, 53: 633-41; Yu et al., Cancer Res, 2004, 64: 4973-9) using dendritic cells from patients who have their pancreatic tumor resected. The patient's dendritic cells are then loaded ex vivo with his own antigens, that is to say, with the C-terminal glycopeptide(s) of BSDL/FAPP carrying the J28 glycotope(s) (and perhaps also the 16D10 glycotope) obtained from the urine, before being reinjected in the patient to induce an immune response directed against residual tumor foci which express said same antigens.

Said strategy of human dendritic cell activation, currently under evaluation using as tumor antigen the recombinant C-terminal glycopeptide of FAPP carrying the glycosylated J28 epitope (example 10), can also be carried out by using the urinary C-terminal glycopeptide of BSDL/FAPP carrying said glycosylated epitopes. The purification protocols (different steps of centrifugation, ultrafiltration and concentration, combined with liquid chromatography on exclusion and affinity columns) developed in order to purify and characterize BSDL in the urine of healthy individuals are used to purify BSDL/FAPP carrying the J28 glycotope (and also that of 16D10) from urine samples of patients with pancreatic adenocarcinoma. The protocol is as follows: Native urine is centrifuged to eliminate cellular debris and partially desalted by ultrafiltration on a Centripreps® YM-10, then completely desalted on a Sephadex® G-25 column. The recovered fractions are lyophilized, then taken up in 10 mM Tris-HCl elution buffer, pH 7.8, 400 mM NaCl, and loaded on Sephacryl™ S-200 gel to separate the proteins according to their molecular mass. Fractions containing BSDL/FAPP carrying the J28 glycotope (and/or the 16D10 glycotype) are collected, dialyzed and lyophilized. The lyophilizates obtained after molecular sieving are rehydrated in PBS, and BSDL/FAPP carrying the J28 glycotope (and perhaps also the 16D10 glycotope) is purified either by immunoaffinity chromatography on an agarose-mAbJ28 column or on a heparin Sepharose column. Purified BSDL/FAPP carrying the J28 glycotope (and/or the 16D10 glycotype) is digested with trypsin or cyanogen bromide to obtain the C-terminal glycopeptide of BSDL/FAPP carrying said glycotopes, as described elsewhere to isolate the C-terminal domain of BSDL/FAPP (Mas et al., 1997, Glycobiology, 7: 745-752). The dendritic cells of patients with pancreatic adenocarcinoma are cultured in the presence of said glycopeptide carrying the J28 glycotope (and/or the 16D10 glycotype) purified from their own urine. The presence of the glycopeptides at the surface of the pulsed mature dendritic cells will be checked by confocal microscopy before the cells are reinjected in the patient to induce an anti-tumor response.

The invention claimed is:

1. A monoclonal antibody selected from the group consisting of monoclonal antibody 16D10 or an antigen binding fragment thereof, having binding specificity for glycosylated bile salt dependent lipase (BSDL) or fetoacinar pancreatic protein (FAPP) and produced by the hybridoma deposited under the accession number I-3188; a monoclonal antibody, or an antigen binding fragment thereof, which binds to the same epitope of the BSDL or FAPP protein as monoclonal antibody 16D10; and a derivative of the 16D10 monoclonal antibody selected from the group consisting of a chimeric 16D10, humanized 16D10 or single chain scFv 16D10 antibody.

2. The monoclonal antibody according to claim 1, wherein said derivative of the 16D10 monoclonal antibody is humanized 16D10 or chimeric 16D10.

3. The monoclonal antibody according to claim 1, wherein the monoclonal antibody is of the IgG type.

4. The monoclonal antibody according to claim 1, wherein the derivative of monoclonal antibody 16D10 is a single chain scFv 16D10 antibody.

5. A kit for diagnosis of a pancreatic pathology, comprising a monoclonal antibody according to claim 1 and a means for detecting the immunological complex resulting from the immunological reaction between the biological sample and said antibody.

6. A method of detection in vitro of a subject suffering from a pancreatic pathology, comprising contacting a biological sample from the subject with monoclonal antibody according to claim 1 and detecting the formation of immunological complexes resulting from the immunological reaction between said antibody and said biological sample.

7. The method according to claim 6, wherein said biological sample is a sample of pancreatic tissue.

8. The method according to claim 6, wherein said biological sample is a biological fluid selected from pancreatic juices, serum or urine.

9. The method according to claim 6, wherein the method enables the detection of a subject suffering from pancreatic cancer.

10. The monoclonal antibody according to claim 2, wherein said derivative of the 16D10 monoclonal antibody is humanized 16D10.

11. The monoclonal antibody according to claim 2, wherein said derivative of the 16D10 monoclonal antibody is chimeric 16D10.

12. The monoclonal antibody according to claim 1, wherein said monoclonal antibody is the 16D10 antibody, having binding specificity for glycosylated bile salt dependent lipase (BSDL) or fetoacinar pancreatic protein (FAPP) and produced by the hybridoma deposited under the accession number I-3188.

13. The monoclonal antibody according to claim 1, wherein said monoclonal antibody is an antigen binding fragment of the 16D10 antibody.

14. The monoclonal antibody according to claim 1, wherein said monoclonal antibody is a single chain scFv antibody.

15. The monoclonal antibody according to claim 1, further comprising a label.

16. A composition comprising a pharmaceutically acceptable excipient and a labeled or unlabeled monoclonal antibody selected from the group consisting of: monoclonal antibody 16D10, or an antigen binding fragment thereof, having binding specificity for glycosylated bile salt dependent lipase (BSDL) or fetoacinar pancreatic protein (FAPP) and produced by the hybridoma deposited under the accession number I-3188; a monoclonal antibody, or an antigen binding fragment thereof, which binds to the same epitope of the BSDL or FAPP protein as monoclonal antibody 16D10; and a derivative of the 16D10 antibody selected from the group consisting of a chimeric 16D10, humanized 16D10 or single chain scFv 16D10 antibody.

17. The composition according to claim 16, wherein said labeled or unlabeled derivative of the 16D10 monoclonal antibody is humanized 16D10 or chimeric 16D10.

18. The composition according to claim 16, wherein the labeled or unlabeled monoclonal antibody is of the IgG type.

19. The composition according to claim 16, wherein the labeled or unlabeled monoclonal antibody is a derivative of the 16D10 antibody that is a single chain scFv 16D10 antibody.

20. The composition according to claim 17, wherein said labeled or unlabeled derivative of monoclonal antibody is 16D10 is humanized 16D10.

21. The composition according to claim 17, wherein said labeled or unlabeled derivative or monoclonal antibody is 16D10 is chimeric 16D10.

22. The composition according to claim 16, wherein said labeled or unlabeled monoclonal antibody is the 16D10 antibody, having binding specificity for glycosylated bile salt dependent lipase (BSDL) or human fetoacinar pancreatic protein (FAPP) and produced by the hybridoma deposited under the accession number I-3188.

23. The composition according to claim 16, wherein said labeled or unlabeled monoclonal antibody is an antigen binding fragment of the 16D10 antibody.

24. The composition according to claim 16, wherein said labeled or unlabeled monoclonal antibody is a single chain scFv antibody.

25. A hybridoma producing the monoclonal antibody is the 16D10 antibody, said hybridoma deposited under the accession number I-3188 and said antibody having binding specificity for glycosylated bile salt dependent lipase (BSDL) or fetoacinar pancreatic protein (FAPP).

26. The composition according to claim 16, wherein said monoclonal antibody is a monoclonal antibody, or an antigen binding fragment thereof, which binds to the same epitope of the BSDL or FAPP protein as monoclonal antibody 16D10.

27. The monoclonal antibody according to claim 1, wherein said monoclonal antibody is a monoclonal antibody, or an antigen binding fragment thereof, which binds to the same epitope of the BSDL or FAPP protein as monoclonal antibody 16D10.

* * * * *

UNITED STATES PATENT AND TRADEMARK OFFICE
CERTIFICATE OF CORRECTION

PATENT NO. : 7,557,193 B2
APPLICATION NO. : 10/593859
DATED : July 7, 2009
INVENTOR(S) : Dominique Lombardo et al.

It is certified that error appears in the above-identified patent and that said Letters Patent is hereby corrected as shown below:

Column 17,
Line 36, "ma16D10" should read --mAb16D10--.

Column 18,
Line 57, "1089 Phe364" should read --1089: Phe364--.

Column 20,
Line 13, "B) Bacterial Transformation" should read --b) Bacterial Transformation--.
Line 26, "C) Plasmid Purification" should read --c) Plasmid Purification--.

Column 25,
Line 34, "NaCl/50 µl" should read --NaCl/150 µl--.

Column 27,
Line 9, "1089 Phe364" should read --1089: Phe364--.
Line 22, "prepared" should read --prepared:--.

Column 62,
Lines 34-35, "antibody is 16D10 is humanized" should read
   --antibody 16D10 is humanized--.
Lines 37-38, "derivative or monoclonal antibody is 16D10 is chimeric" should read
   --derivative of monoclonal antibody 16D10 is chimeric--.

Signed and Sealed this

Eighth Day of September, 2009

David J. Kappos
*Director of the United States Patent and Trademark Office*

SEQUENCE LISTING

<160> NUMBER OF SEQ ID NOS: 14

<210> SEQ ID NO 1
<211> LENGTH: 36
<212> TYPE: DNA
<213> ORGANISM: Homo sapiens

<400> SEQUENCE: 1
ttcgtaagct tgcgaagctg ggcgccgtgt acagaa                36

<210> SEQ ID NO 2
<211> LENGTH: 42
<212> TYPE: DNA
<213> ORGANISM: Homo sapiens

<400> SEQUENCE: 2
tttcgtgaat tcacgctaaa acctaatgac tgcaggcatc tg         42

<210> SEQ ID NO 3
<211> LENGTH: 33
<212> TYPE: DNA
<213> ORGANISM: Homo sapiens

<400> SEQUENCE: 3
cgtctaaagc tttttgatgt ctacaccgag tcc                   33

<210> SEQ ID NO 4
<211> LENGTH: 27
<212> TYPE: DNA
<213> ORGANISM: Homo sapiens

<400> SEQUENCE: 4
aaaaagaatt cggagaaaat aatgaat                          27

<210> SEQ ID NO 5
<211> LENGTH: 28
<212> TYPE: DNA
<213> ORGANISM: Homo sapiens

<400> SEQUENCE: 5
aaaaagggcc cacaaagtca gacattat                         28

<210> SEQ ID NO 6
<211> LENGTH: 2350
<212> TYPE: DNA
<213> ORGANISM: Homo sapiens
<220> FEATURE:
<221> NAME/KEY: CDS
<222> LOCATION: (17)..(2251)

<400> SEQUENCE: 6
ggccacccag aggctg atg ctc acc atg ggg cgc ctg caa ctg gtt gtg ttg    52
                 Met Leu Thr Met Gly Arg Leu Gln Leu Val Val Leu
                  1               5                  10 ggc ctc acc tgc tgc tgg gca gtg gcg agt gcc gcg aag ctg ggc gcc    100
Gly Leu Thr Cys Cys Trp Ala Val Ala Ser Ala Ala Lys Leu Gly Ala
         15                  20                  25 gtg tac aca gaa ggt ggg ttc gtg gaa ggc gtc aat aag aag ctc ggc    148
Val Tyr Thr Glu Gly Gly Phe Val Glu Gly Val Asn Lys Lys Leu Gly
     30                  35                  40

```
ctc ctg ggt gac tct gtg gac atc ttc aag ggc atc ccc ttc gca gct       196
Leu Leu Gly Asp Ser Val Asp Ile Phe Lys Gly Ile Pro Phe Ala Ala
 45              50                  55                  60 ccc acc aag gcc ctg gaa aat cct cag cca cat cct ggc tgg caa ggg       244
Pro Thr Lys Ala Leu Glu Asn Pro Gln Pro His Pro Gly Trp Gln Gly
                 65                  70                  75 acc ctg aag gcc aag aac ttc aag aag aga tgc ctg cag gcc acc atc       292
Thr Leu Lys Ala Lys Asn Phe Lys Lys Arg Cys Leu Gln Ala Thr Ile
             80                  85                  90 acc cag gac agc acc tac ggg gat gaa gac tgc ctg tac ctc aac att       340
Thr Gln Asp Ser Thr Tyr Gly Asp Glu Asp Cys Leu Tyr Leu Asn Ile
         95                 100                 105 tgg gtg ccc cag ggc agg aag caa gtc tcc cgg gac ctg ccc gtt atg       388
Trp Val Pro Gln Gly Arg Lys Gln Val Ser Arg Asp Leu Pro Val Met
     110                 115                 120 atc tgg atc tat gga ggc gcc ttc ctc atg ggg tcc ggc cat ggg gcc       436
Ile Trp Ile Tyr Gly Gly Ala Phe Leu Met Gly Ser Gly His Gly Ala
125                 130                 135                 140 aac ttc ctc aac aac tac ctg tat gac ggc gag gag atc gcc aca cgc       484
Asn Phe Leu Asn Asn Tyr Leu Tyr Asp Gly Glu Glu Ile Ala Thr Arg
                145                 150                 155 gga aac gtc atc gtg gtc acc ttc aac tac cgt gtc ggc ccc ctt ggg       532
Gly Asn Val Ile Val Val Thr Phe Asn Tyr Arg Val Gly Pro Leu Gly
            160                 165                 170 ttc ctc agc act ggg gac gcc aat ctg cca ggt aac tat ggc ctt cgg       580
Phe Leu Ser Thr Gly Asp Ala Asn Leu Pro Gly Asn Tyr Gly Leu Arg
        175                 180                 185 gat cag cac atg gcc att gct tgg gtg aag agg aat atc gcg gcc ttc       628
Asp Gln His Met Ala Ile Ala Trp Val Lys Arg Asn Ile Ala Ala Phe
    190                 195                 200 ggg ggg gac ccc aac aac atc acg ctc ttc ggg gag tct gct gga ggt       676
Gly Gly Asp Pro Asn Asn Ile Thr Leu Phe Gly Glu Ser Ala Gly Gly
205                 210                 215                 220 gcc agc gtc tct ctg cag acc ctc tcc ccc tac aac aag ggc ctc atc       724
Ala Ser Val Ser Leu Gln Thr Leu Ser Pro Tyr Asn Lys Gly Leu Ile
                225                 230                 235 cgg cga gcc atc agc cag agc ggc gtg gcc ctg agt ccc tgg gtc atc       772
Arg Arg Ala Ile Ser Gln Ser Gly Val Ala Leu Ser Pro Trp Val Ile
            240                 245                 250 cag aaa aac cca ctc ttc tgg gcc aaa aag gtg gct gag aag gtg ggt       820
Gln Lys Asn Pro Leu Phe Trp Ala Lys Lys Val Ala Glu Lys Val Gly
        255                 260                 265 tgc cct gtg ggt gat gcc gcc agg atg gcc cag tgt ctg aag gtt act       868
Cys Pro Val Gly Asp Ala Ala Arg Met Ala Gln Cys Leu Lys Val Thr
    270                 275                 280 gat ccc cga gcc ctg acg ctg gcc tat aag gtg ccg ctg gca ggc ctg       916
Asp Pro Arg Ala Leu Thr Leu Ala Tyr Lys Val Pro Leu Ala Gly Leu
285                 290                 295                 300 gag tac ccc atg ctg cac tat gtg ggc ttc gtc cct gtc att gat gga       964
Glu Tyr Pro Met Leu His Tyr Val Gly Phe Val Pro Val Ile Asp Gly
                305                 310                 315 gac ttc atc ccc gct gac ccg atc aac ctg tac gcc aac gcc gcc gac      1012
Asp Phe Ile Pro Ala Asp Pro Ile Asn Leu Tyr Ala Asn Ala Ala Asp
            320                 325                 330 atc gac tat ata gca ggc acc aac aac atg gac ggc cac atc ttc gcc      1060
Ile Asp Tyr Ile Ala Gly Thr Asn Asn Met Asp Gly His Ile Phe Ala
        335                 340                 345 agc atc gac atg cct gcc atc aac aag ggc aac aag aaa gtc acg gag      1108
Ser Ile Asp Met Pro Ala Ile Asn Lys Gly Asn Lys Lys Val Thr Glu
    350                 355                 360
```

-continued

| | |
|---|---|
| gag gac ttc tac aag ctg gtc agt gag ttc aca atc acc aag ggg ctc<br>Glu Asp Phe Tyr Lys Leu Val Ser Glu Phe Thr Ile Thr Lys Gly Leu<br>365                 370                 375                 380 | 1156 |
| aga ggc gcc aag acg acc ttt gat gtc tac acc gag tcc tgg gcc cag<br>Arg Gly Ala Lys Thr Thr Phe Asp Val Tyr Thr Glu Ser Trp Ala Gln<br>                385                 390                 395 | 1204 |
| gac cca tcc cag gag aat aag aag aag act gtg gtg gac ttt gag acc<br>Asp Pro Ser Gln Glu Asn Lys Lys Lys Thr Val Val Asp Phe Glu Thr<br>400                 405                 410 | 1252 |
| gat gtc ctc ttc ctg gtg ccc acc gag att gcc cta gcc cag cac aga<br>Asp Val Leu Phe Leu Val Pro Thr Glu Ile Ala Leu Ala Gln His Arg<br>                415                 420                 425 | 1300 |
| gcc aat gcc aag agt gcc aag acc tac gcc tac ctg ttt tcc cat ccc<br>Ala Asn Ala Lys Ser Ala Lys Thr Tyr Ala Tyr Leu Phe Ser His Pro<br>430                 435                 440 | 1348 |
| tct cgg atg ccc gtc tac ccc aaa tgg gtg ggg gcc gac cat gca gat<br>Ser Arg Met Pro Val Tyr Pro Lys Trp Val Gly Ala Asp His Ala Asp<br>445                 450                 455                 460 | 1396 |
| gac att cag tac gtt ttc ggg aag ccc ttc gcc acc ccc acg ggc tac<br>Asp Ile Gln Tyr Val Phe Gly Lys Pro Phe Ala Thr Pro Thr Gly Tyr<br>                465                 470                 475 | 1444 |
| cgg ccc caa gac agg aca gtc tct aag gcc atg atc gcc tac tgg acc<br>Arg Pro Gln Asp Arg Thr Val Ser Lys Ala Met Ile Ala Tyr Trp Thr<br>                480                 485                 490 | 1492 |
| aac ttt gcc aaa aca ggg gac ccc aac atg ggc gac tcg gct gtg ccc<br>Asn Phe Ala Lys Thr Gly Asp Pro Asn Met Gly Asp Ser Ala Val Pro<br>                495                 500                 505 | 1540 |
| aca cac tgg gaa ccc tac act acg gaa aac agc ggc tac ctg gag atc<br>Thr His Trp Glu Pro Tyr Thr Thr Glu Asn Ser Gly Tyr Leu Glu Ile<br>510                 515                 520 | 1588 |
| acc aag aag atg ggc agc agc tcc atg aag cgg agc ctg aga acc aac<br>Thr Lys Lys Met Gly Ser Ser Ser Met Lys Arg Ser Leu Arg Thr Asn<br>525                 530                 535                 540 | 1636 |
| ttc ctg cgc tac tgg acc ctc acc tat ctg gcg ctg ccc aca gtg acc<br>Phe Leu Arg Tyr Trp Thr Leu Thr Tyr Leu Ala Leu Pro Thr Val Thr<br>                545                 550                 555 | 1684 |
| gac cag gag gcc acc cct gtg ccc ccc aca ggg gac tcc gag gcc act<br>Asp Gln Glu Ala Thr Pro Val Pro Pro Thr Gly Asp Ser Glu Ala Thr<br>                560                 565                 570 | 1732 |
| ccc gtg ccc ccc acg ggt gac tcc gag acc gcc ccc gtg ccg ccc acg<br>Pro Val Pro Pro Thr Gly Asp Ser Glu Thr Ala Pro Val Pro Pro Thr<br>                575                 580                 585 | 1780 |
| ggt gac tcc ggg gcc ccc ccc gtg ccg ccc acg ggt gac tcc ggg gcc<br>Gly Asp Ser Gly Ala Pro Pro Val Pro Pro Thr Gly Asp Ser Gly Ala<br>590                 595                 600 | 1828 |
| ccc ccc gtg ccg ccc acg ggt gac tcc ggg gcc ccc ccc gtg ccg ccc<br>Pro Pro Val Pro Pro Thr Gly Asp Ser Gly Ala Pro Pro Val Pro Pro<br>605                 610                 615                 620 | 1876 |
| acg ggt gac tcc ggg gcc ccc ccc gtg ccg ccc acg ggt gac tcc ggg<br>Thr Gly Asp Ser Gly Ala Pro Pro Val Pro Pro Thr Gly Asp Ser Gly<br>                625                 630                 635 | 1924 |
| gcc ccc ccc gtg ccg ccc acg ggt gac tcc ggg gcc ccc ccc gtg ccg<br>Ala Pro Pro Val Pro Pro Thr Gly Asp Ser Gly Ala Pro Pro Val Pro<br>                640                 645                 650 | 1972 |
| ccc acg ggt gac tcc ggc gcc ccc ccc gtg ccg ccc acg ggt gac gcc<br>Pro Thr Gly Asp Ser Gly Ala Pro Pro Val Pro Pro Thr Gly Asp Ala<br>                655                 660                 665 | 2020 |
| ggg ccc ccc ccc gtg ccg ccc acg ggt gac tcc ggc gcc ccc ccc gtg<br>Gly Pro Pro Pro Val Pro Pro Thr Gly Asp Ser Gly Ala Pro Pro Val<br>670                 675                 680 | 2068 |

-continued

```
ccg ccc acg ggt gac tcc ggg gcc ccc ccc gtg acc ccc acg ggt gac    2116
Pro Pro Thr Gly Asp Ser Gly Ala Pro Pro Val Thr Pro Thr Gly Asp
685                 690                 695                 700 tcc gag acc gcc ccc gtg ccg ccc acg ggt gac tcc ggg gcc ccc cct    2164
Ser Glu Thr Ala Pro Val Pro Pro Thr Gly Asp Ser Gly Ala Pro Pro
            705                 710                 715 gtg ccc ccc acg ggt gac tct gag gct gcc cct gtg ccc ccc aca gat    2212
Val Pro Pro Thr Gly Asp Ser Glu Ala Ala Pro Val Pro Pro Thr Asp
        720                 725                 730 gac tcc aag gaa gct cag atg cct gca gtc att agg ttt tagcgtccca    2261
Asp Ser Lys Glu Ala Gln Met Pro Ala Val Ile Arg Phe
    735                 740                 745 tgagccttgg tatcaagagg ccacaagagt gggaccccag gggctcccct cccatcttga    2321
gctcttcctg aataaagcct cataccct                                       2350

<210> SEQ ID NO 7
<211> LENGTH: 745
<212> TYPE: PRT
<213> ORGANISM: Homo sapiens

<400> SEQUENCE: 7

Met Leu Thr Met Gly Arg Leu Gln Leu Val Val Gly Leu Thr Cys
1               5                   10                  15

Cys Trp Ala Val Ala Ser Ala Ala Lys Leu Gly Ala Val Tyr Thr Glu
                20                  25                  30

Gly Gly Phe Val Glu Gly Val Asn Lys Lys Leu Gly Leu Leu Gly Asp
            35                  40                  45

Ser Val Asp Ile Phe Lys Gly Ile Pro Phe Ala Ala Pro Thr Lys Ala
    50                  55                  60

Leu Glu Asn Pro Gln Pro His Pro Gly Trp Gln Gly Thr Leu Lys Ala
65                  70                  75                  80

Lys Asn Phe Lys Lys Arg Cys Leu Gln Ala Thr Ile Thr Gln Asp Ser
                85                  90                  95

Thr Tyr Gly Asp Glu Asp Cys Leu Tyr Leu Asn Ile Trp Val Pro Gln
            100                 105                 110

Gly Arg Lys Gln Val Ser Arg Asp Leu Pro Val Met Ile Trp Ile Tyr
        115                 120                 125

Gly Gly Ala Phe Leu Met Gly Ser Gly His Gly Ala Asn Phe Leu Asn
    130                 135                 140

Asn Tyr Leu Tyr Asp Gly Glu Glu Ile Ala Thr Arg Gly Asn Val Ile
145                 150                 155                 160

Val Val Thr Phe Asn Tyr Arg Val Gly Pro Leu Gly Phe Leu Ser Thr
                165                 170                 175

Gly Asp Ala Asn Leu Pro Gly Asn Tyr Gly Leu Arg Asp Gln His Met
            180                 185                 190

Ala Ile Ala Trp Val Lys Arg Asn Ile Ala Ala Phe Gly Gly Asp Pro
        195                 200                 205

Asn Asn Ile Thr Leu Phe Gly Glu Ser Ala Gly Gly Ala Ser Val Ser
    210                 215                 220

Leu Gln Thr Leu Ser Pro Tyr Asn Lys Gly Leu Ile Arg Arg Ala Ile
225                 230                 235                 240

Ser Gln Ser Gly Val Ala Leu Ser Pro Trp Val Ile Gln Lys Asn Pro
                245                 250                 255

Leu Phe Trp Ala Lys Lys Val Ala Glu Lys Val Gly Cys Pro Val Gly
            260                 265                 270
```

-continued

```
Asp Ala Ala Arg Met Ala Gln Cys Leu Lys Val Thr Asp Pro Arg Ala
        275                 280                 285
Leu Thr Leu Ala Tyr Lys Val Pro Leu Ala Gly Leu Glu Tyr Pro Met
    290                 295                 300
Leu His Tyr Val Gly Phe Val Pro Val Ile Asp Gly Asp Phe Ile Pro
305                 310                 315                 320
Ala Asp Pro Ile Asn Leu Tyr Ala Asn Ala Ala Asp Ile Asp Tyr Ile
                325                 330                 335
Ala Gly Thr Asn Asn Met Asp Gly His Ile Phe Ala Ser Ile Asp Met
            340                 345                 350
Pro Ala Ile Asn Lys Gly Asn Lys Val Thr Glu Glu Asp Phe Tyr
        355                 360                 365
Lys Leu Val Ser Glu Phe Thr Ile Thr Lys Gly Leu Arg Gly Ala Lys
    370                 375                 380
Thr Thr Phe Asp Val Tyr Thr Glu Ser Trp Ala Gln Asp Pro Ser Gln
385                 390                 395                 400
Glu Asn Lys Lys Lys Thr Val Val Asp Phe Glu Thr Asp Val Leu Phe
                405                 410                 415
Leu Val Pro Thr Glu Ile Ala Leu Ala Gln His Arg Ala Asn Ala Lys
            420                 425                 430
Ser Ala Lys Thr Tyr Ala Tyr Leu Phe Ser His Pro Ser Arg Met Pro
        435                 440                 445
Val Tyr Pro Lys Trp Val Gly Ala Asp His Ala Asp Asp Ile Gln Tyr
    450                 455                 460
Val Phe Gly Lys Pro Phe Ala Thr Pro Thr Gly Tyr Arg Pro Gln Asp
465                 470                 475                 480
Arg Thr Val Ser Lys Ala Met Ile Ala Tyr Trp Thr Asn Phe Ala Lys
                485                 490                 495
Thr Gly Asp Pro Asn Met Gly Asp Ser Ala Val Pro Thr His Trp Glu
            500                 505                 510
Pro Tyr Thr Thr Glu Asn Ser Gly Tyr Leu Glu Ile Thr Lys Lys Met
        515                 520                 525
Gly Ser Ser Ser Met Lys Arg Ser Leu Arg Thr Asn Phe Leu Arg Tyr
    530                 535                 540
Trp Thr Leu Thr Tyr Leu Ala Leu Pro Thr Val Thr Asp Gln Glu Ala
545                 550                 555                 560
Thr Pro Val Pro Pro Thr Gly Asp Ser Glu Ala Thr Pro Val Pro Pro
                565                 570                 575
Thr Gly Asp Ser Glu Thr Ala Pro Val Pro Pro Thr Gly Asp Ser Gly
            580                 585                 590
Ala Pro Pro Val Pro Pro Thr Gly Asp Ser Gly Ala Pro Pro Val Pro
        595                 600                 605
Pro Thr Gly Asp Ser Gly Ala Pro Pro Val Pro Pro Thr Gly Asp Ser
    610                 615                 620
Gly Ala Pro Pro Val Pro Pro Thr Gly Asp Ser Gly Ala Pro Pro Val
625                 630                 635                 640
Pro Pro Thr Gly Asp Ser Gly Ala Pro Pro Val Pro Pro Thr Gly Asp
                645                 650                 655
Ser Gly Ala Pro Pro Val Pro Pro Thr Gly Asp Ala Gly Pro Pro Pro
            660                 665                 670
Val Pro Pro Thr Gly Asp Ser Gly Ala Pro Pro Val Pro Pro Thr Gly
        675                 680                 685
```

```
Asp Ser Gly Ala Pro Pro Val Thr Pro Thr Gly Asp Ser Glu Thr Ala
    690                 695                 700

Pro Val Pro Pro Thr Gly Asp Ser Gly Ala Pro Val Pro Pro Thr
705                 710                 715                 720

Gly Asp Ser Glu Ala Ala Pro Val Pro Pro Thr Asp Asp Ser Lys Glu
                725                 730                 735

Ala Gln Met Pro Ala Val Ile Arg Phe
            740                 745

<210> SEQ ID NO 8
<211> LENGTH: 1083
<212> TYPE: DNA
<213> ORGANISM: Homo sapiens
<220> FEATURE:
<221> NAME/KEY: CDS
<222> LOCATION: (1)..(1077)

<400> SEQUENCE: 8
```

| | | | | | | | | | | | | | | | | |
|---|---|---|---|---|---|---|---|---|---|---|---|---|---|---|---|---|
| ttt | gat | gtc | tac | acc | gag | tcc | tgg | gcc | cag | gac | cca | tcc | cag | gag | aat | 48 |
| Phe | Asp | Val | Tyr | Thr | Glu | Ser | Trp | Ala | Gln | Asp | Pro | Ser | Gln | Glu | Asn | |
| 1 | | | | 5 | | | | | 10 | | | | | 15 | | |
| aag | aag | aag | act | gtg | gtg | gac | ttt | gag | acc | gat | gtc | ctc | ttc | ctg | gtg | 96 |
| Lys | Lys | Lys | Thr | Val | Val | Asp | Phe | Glu | Thr | Asp | Val | Leu | Phe | Leu | Val | |
| | | | 20 | | | | | 25 | | | | | 30 | | | |
| ccc | acc | gag | att | gcc | cta | gcc | cag | cac | aga | gcc | aat | gcc | aag | agt | gcc | 144 |
| Pro | Thr | Glu | Ile | Ala | Leu | Ala | Gln | His | Arg | Ala | Asn | Ala | Lys | Ser | Ala | |
| | | 35 | | | | | 40 | | | | | 45 | | | | |
| aag | acc | tac | gcc | tac | ctg | ttt | tcc | cat | ccc | tct | cgg | atg | ccc | gtc | tac | 192 |
| Lys | Thr | Tyr | Ala | Tyr | Leu | Phe | Ser | His | Pro | Ser | Arg | Met | Pro | Val | Tyr | |
| | 50 | | | | | 55 | | | | | 60 | | | | | |
| ccc | aaa | tgg | gtg | ggg | gcc | gac | cat | gca | gat | gac | att | cag | tac | gtt | ttc | 240 |
| Pro | Lys | Trp | Val | Gly | Ala | Asp | His | Ala | Asp | Asp | Ile | Gln | Tyr | Val | Phe | |
| 65 | | | | | 70 | | | | | 75 | | | | | 80 | |
| ggg | aag | ccc | ttc | gcc | acc | ccc | acg | ggc | tac | cgg | ccc | caa | gac | agg | aca | 288 |
| Gly | Lys | Pro | Phe | Ala | Thr | Pro | Thr | Gly | Tyr | Arg | Pro | Gln | Asp | Arg | Thr | |
| | | | | 85 | | | | | 90 | | | | | 95 | | |
| gtc | tct | aag | gcc | atg | atc | gcc | tac | tgg | acc | aac | ttt | gcc | aaa | aca | ggg | 336 |
| Val | Ser | Lys | Ala | Met | Ile | Ala | Tyr | Trp | Thr | Asn | Phe | Ala | Lys | Thr | Gly | |
| | | | 100 | | | | | 105 | | | | | 110 | | | |
| gac | ccc | aac | atg | ggc | gac | tcg | gct | gtg | ccc | aca | cac | tgg | gaa | ccc | tac | 384 |
| Asp | Pro | Asn | Met | Gly | Asp | Ser | Ala | Val | Pro | Thr | His | Trp | Glu | Pro | Tyr | |
| | | 115 | | | | | 120 | | | | | 125 | | | | |
| act | acg | gaa | aac | agc | ggc | tac | ctg | gag | atc | acc | aag | aag | atg | ggc | agc | 432 |
| Thr | Thr | Glu | Asn | Ser | Gly | Tyr | Leu | Glu | Ile | Thr | Lys | Lys | Met | Gly | Ser | |
| | 130 | | | | | 135 | | | | | 140 | | | | | |
| agc | tcc | atg | aag | cgg | agc | ctg | aga | acc | aac | ttc | ctg | cgc | tac | tgg | acc | 480 |
| Ser | Ser | Met | Lys | Arg | Ser | Leu | Arg | Thr | Asn | Phe | Leu | Arg | Tyr | Trp | Thr | |
| 145 | | | | | 150 | | | | | 155 | | | | | 160 | |
| ctc | acc | tat | ctg | gcg | ctg | ccc | aca | gtg | acc | gac | cag | gag | gcc | acc | cct | 528 |
| Leu | Thr | Tyr | Leu | Ala | Leu | Pro | Thr | Val | Thr | Asp | Gln | Glu | Ala | Thr | Pro | |
| | | | | 165 | | | | | 170 | | | | | 175 | | |
| gtg | ccc | ccc | aca | ggg | gac | tcc | gag | gcc | act | ccc | gtg | ccc | ccc | acg | ggt | 576 |
| Val | Pro | Pro | Thr | Gly | Asp | Ser | Glu | Ala | Thr | Pro | Val | Pro | Pro | Thr | Gly | |
| | | | 180 | | | | | 185 | | | | | 190 | | | |
| gac | tcc | gag | acc | gcc | ccc | gtg | ccg | ccc | acg | ggt | gac | tcc | ggg | gcc | ccc | 624 |
| Asp | Ser | Glu | Thr | Ala | Pro | Val | Pro | Pro | Thr | Gly | Asp | Ser | Gly | Ala | Pro | |
| | | 195 | | | | | 200 | | | | | 205 | | | | |
| ccc | gtg | ccg | ccc | acg | ggt | gac | tcc | ggg | gcc | ccc | ccc | gtg | ccg | ccc | acg | 672 |
| Pro | Val | Pro | Pro | Thr | Gly | Asp | Ser | Gly | Ala | Pro | Pro | Val | Pro | Pro | Thr | |
| | 210 | | | | | 215 | | | | | 220 | | | | | |

-continued

```
ggt gac tcc ggg gcc ccc ccc gtg ccg ccc acg ggt gac tcc ggg gcc    720
Gly Asp Ser Gly Ala Pro Pro Val Pro Pro Thr Gly Asp Ser Gly Ala
225                 230                 235                 240 ccc ccc gtg ccg ccc acg ggt gac tcc ggg gcc ccc ccc gtg ccg ccc    768
Pro Pro Val Pro Pro Thr Gly Asp Ser Gly Ala Pro Pro Val Pro Pro
                245                 250                 255 acg ggt gac tcc ggg gcc ccc ccc gtg ccg ccc acg ggt gac tcc ggc    816
Thr Gly Asp Ser Gly Ala Pro Pro Val Pro Pro Thr Gly Asp Ser Gly
            260                 265                 270 gcc ccc ccc gtg ccg ccc acg ggt gac gcc ggg ccc ccc gtg ccg        864
Ala Pro Pro Val Pro Pro Thr Gly Asp Ala Gly Pro Pro Val Pro
        275                 280                 285 ccc acg ggt gac tcc ggc gcc ccc gtg ccg ccc acg ggt gac tcc        912
Pro Thr Gly Asp Ser Gly Ala Pro Pro Val Pro Pro Thr Gly Asp Ser
    290                 295                 300 ggg gcc ccc ccc gtg acc ccc acg ggt gac tcc gag acc gcc ccc gtg    960
Gly Ala Pro Pro Val Thr Pro Thr Gly Asp Ser Glu Thr Ala Pro Val
305                 310                 315                 320 ccg ccc acg ggt gac tcc ggg gcc ccc cct gtg ccc ccc acg ggt gac   1008
Pro Pro Thr Gly Asp Ser Gly Ala Pro Pro Val Pro Pro Thr Gly Asp
                325                 330                 335 tct gag gct gcc cct gtg ccc ccc aca gat gac tcc aag gaa gct cag   1056
Ser Glu Ala Ala Pro Val Pro Pro Thr Asp Asp Ser Lys Glu Ala Gln
            340                 345                 350 atg cct gca gtc att agg ttt tagcgt                                 1083
Met Pro Ala Val Ile Arg Phe
        355
```

<210> SEQ ID NO 9
<211> LENGTH: 359
<212> TYPE: PRT
<213> ORGANISM: Homo sapiens

<400> SEQUENCE: 9

```
Phe Asp Val Tyr Thr Glu Ser Trp Ala Gln Asp Pro Ser Gln Glu Asn
1               5                   10                  15

Lys Lys Lys Thr Val Val Asp Phe Glu Thr Asp Val Leu Phe Leu Val
            20                  25                  30

Pro Thr Glu Ile Ala Leu Ala Gln His Arg Ala Asn Ala Lys Ser Ala
        35                  40                  45

Lys Thr Tyr Ala Tyr Leu Phe Ser His Pro Ser Arg Met Pro Val Tyr
    50                  55                  60

Pro Lys Trp Val Gly Ala Asp His Ala Asp Asp Ile Gln Tyr Val Phe
65                  70                  75                  80

Gly Lys Pro Phe Ala Thr Pro Thr Gly Tyr Arg Pro Gln Asp Arg Thr
                85                  90                  95

Val Ser Lys Ala Met Ile Ala Tyr Trp Thr Asn Phe Ala Lys Thr Gly
            100                 105                 110

Asp Pro Asn Met Gly Asp Ser Ala Val Pro Thr His Trp Glu Pro Tyr
        115                 120                 125

Thr Thr Glu Asn Ser Gly Tyr Leu Glu Ile Thr Lys Lys Met Gly Ser
    130                 135                 140

Ser Ser Met Lys Arg Ser Leu Arg Thr Asn Phe Leu Arg Tyr Trp Thr
145                 150                 155                 160

Leu Thr Tyr Leu Ala Leu Pro Thr Val Thr Asp Gln Glu Ala Thr Pro
                165                 170                 175

Val Pro Pro Thr Gly Asp Ser Glu Ala Thr Pro Val Pro Pro Thr Gly
            180                 185                 190
```

-continued

```
Asp Ser Glu Thr Ala Pro Val Pro Pro Thr Gly Asp Ser Gly Ala Pro
        195                 200                 205
Pro Val Pro Pro Thr Gly Asp Ser Gly Ala Pro Pro Val Pro Pro Thr
    210                 215                 220
Gly Asp Ser Gly Ala Pro Pro Val Pro Pro Thr Gly Asp Ser Gly Ala
225                 230                 235                 240
Pro Pro Val Pro Pro Thr Gly Asp Ser Gly Ala Pro Pro Val Pro Pro
            245                 250                 255
Thr Gly Asp Ser Gly Ala Pro Pro Val Pro Pro Thr Gly Asp Ser Gly
        260                 265                 270
Ala Pro Pro Val Pro Pro Thr Gly Asp Ala Gly Pro Pro Val Pro
    275                 280                 285
Pro Thr Gly Asp Ser Gly Ala Pro Pro Val Pro Pro Thr Gly Asp Ser
    290                 295                 300
Gly Ala Pro Pro Val Thr Pro Thr Gly Asp Ser Glu Thr Ala Pro Val
305                 310                 315                 320
Pro Pro Thr Gly Asp Ser Gly Ala Pro Pro Val Pro Pro Thr Gly Asp
            325                 330                 335
Ser Glu Ala Ala Pro Val Pro Pro Thr Asp Asp Ser Lys Glu Ala Gln
        340                 345                 350
Met Pro Ala Val Ile Arg Phe
        355
```

```
<210> SEQ ID NO 10
<211> LENGTH: 1839
<212> TYPE: DNA
<213> ORGANISM: Homo sapiens
<220> FEATURE:
<221> NAME/KEY: CDS
<222> LOCATION: (1)..(1836)

<400> SEQUENCE: 10 gcg aag ctg ggc gcc gtg tac aca gaa ggt ggg ttc gtg gaa ggc gtc      48
Ala Lys Leu Gly Ala Val Tyr Thr Glu Gly Gly Phe Val Glu Gly Val
1               5                   10                  15 aat aag aag ctc ggc ctc ctg ggt gac tct gtg gac atc ttc aag ggc      96
Asn Lys Lys Leu Gly Leu Leu Gly Asp Ser Val Asp Ile Phe Lys Gly
            20                  25                  30 atc ccc ttc gca gct ccc acc aag gcc ctg gaa aat cct cag cca cat     144
Ile Pro Phe Ala Ala Pro Thr Lys Ala Leu Glu Asn Pro Gln Pro His
        35                  40                  45 cct ggc tgg caa ggg acc ctg aag gcc aag aac ttc aag aag aga tgc     192
Pro Gly Trp Gln Gly Thr Leu Lys Ala Lys Asn Phe Lys Lys Arg Cys
    50                  55                  60 ctg cag gcc acc atc acc cag gac agc acc tac ggg gat gaa gac tgc     240
Leu Gln Ala Thr Ile Thr Gln Asp Ser Thr Tyr Gly Asp Glu Asp Cys
65                  70                  75                  80 ctg tac ctc aac att tgg gtg ccc cag ggc agg aag caa gtc tcc cgg     288
Leu Tyr Leu Asn Ile Trp Val Pro Gln Gly Arg Lys Gln Val Ser Arg
                85                  90                  95 gac ctg ccc gtt atg atc tgg atc tat gga ggc gcc ttc ctc atg ggg     336
Asp Leu Pro Val Met Ile Trp Ile Tyr Gly Gly Ala Phe Leu Met Gly
            100                 105                 110 tcc ggc cat ggg gcc aac ttc ctc aac aac tac ctg tat gac ggc gag     384
Ser Gly His Gly Ala Asn Phe Leu Asn Asn Tyr Leu Tyr Asp Gly Glu
        115                 120                 125 gag atc gcc aca cgc gga aac gtc atc gtg gtc acc ttc aac tac cgt     432
Glu Ile Ala Thr Arg Gly Asn Val Ile Val Val Thr Phe Asn Tyr Arg
    130                 135                 140
```

```
gtc ggc ccc ctt ggg ttc ctc agc act ggg gac gcc aat ctg cca ggt     480
Val Gly Pro Leu Gly Phe Leu Ser Thr Gly Asp Ala Asn Leu Pro Gly
145                 150                 155                 160 aac tat ggc ctt cgg gat cag cac atg gcc att gct tgg gtg aag agg     528
Asn Tyr Gly Leu Arg Asp Gln His Met Ala Ile Ala Trp Val Lys Arg
                165                 170                 175 aat atc gcg gcc ttc ggg ggg gac ccc aac aac atc acg ctc ttc ggg     576
Asn Ile Ala Ala Phe Gly Gly Asp Pro Asn Asn Ile Thr Leu Phe Gly
            180                 185                 190 gag tct gct gga ggt gcc agc gtc tct ctg cag act ctc tcc ccc tac     624
Glu Ser Ala Gly Gly Ala Ser Val Ser Leu Gln Thr Leu Ser Pro Tyr
        195                 200                 205 aac aag ggc ctc atc cgg cga gcc atc agc cag agc ggc gtg gcc ctg     672
Asn Lys Gly Leu Ile Arg Arg Ala Ile Ser Gln Ser Gly Val Ala Leu
210                 215                 220 agt ccc tgg gtc atc cag aaa aac cca ctc ttc tgg gcc aaa aag gtg     720
Ser Pro Trp Val Ile Gln Lys Asn Pro Leu Phe Trp Ala Lys Lys Val
225                 230                 235                 240 gct gag aag gtg ggt tgc cct gtg ggt gat gcc gcc agg atg gcc cag     768
Ala Glu Lys Val Gly Cys Pro Val Gly Asp Ala Ala Arg Met Ala Gln
                245                 250                 255 tgt ctg aag gtt act gat ccc cga gcc ctg acg ctg gcc tat aag gtg     816
Cys Leu Lys Val Thr Asp Pro Arg Ala Leu Thr Leu Ala Tyr Lys Val
            260                 265                 270 ccg ctg gca ggc ctg gag tac ccc atg ctg cac tat gtg ggc ttc gtc     864
Pro Leu Ala Gly Leu Glu Tyr Pro Met Leu His Tyr Val Gly Phe Val
        275                 280                 285 cct gtc att gat gga gac ttc atc ccc gct gac ccg atc aac ctg tac     912
Pro Val Ile Asp Gly Asp Phe Ile Pro Ala Asp Pro Ile Asn Leu Tyr
290                 295                 300 gcc aac gcc gcc gac atc gac tat ata gca ggc acc aac aac atg gac     960
Ala Asn Ala Ala Asp Ile Asp Tyr Ile Ala Gly Thr Asn Asn Met Asp
305                 310                 315                 320 ggc cac atc ttc gcc agc atc gac atg cct gcc atc aac aag ggc aac    1008
Gly His Ile Phe Ala Ser Ile Asp Met Pro Ala Ile Asn Lys Gly Asn
                325                 330                 335 aag aaa gtc acg gag gag gac ttc tac aag ctg gtc agt gag ttc aca    1056
Lys Lys Val Thr Glu Glu Asp Phe Tyr Lys Leu Val Ser Glu Phe Thr
            340                 345                 350 atc acc aag ggg ctc aga ggc gcc aag acg acc ttt gat gtc tac acc    1104
Ile Thr Lys Gly Leu Arg Gly Ala Lys Thr Thr Phe Asp Val Tyr Thr
        355                 360                 365 gag tcc tgg gcc cag gac cca tcc cag gag aat aag aag aag act gtg    1152
Glu Ser Trp Ala Gln Asp Pro Ser Gln Glu Asn Lys Lys Lys Thr Val
370                 375                 380 gtg gac ttt gag acc gat gtc ctc ttc ctg gtg ccc acc gag att gcc    1200
Val Asp Phe Glu Thr Asp Val Leu Phe Leu Val Pro Thr Glu Ile Ala
385                 390                 395                 400 cta gcc cag cac aga gcc aat gcc aag agt gcc aag acc tac gcc tac    1248
Leu Ala Gln His Arg Ala Asn Ala Lys Ser Ala Lys Thr Tyr Ala Tyr
                405                 410                 415 ctg ttt tcc cat ccc tct cgg atg ccc gtc tac ccc aaa tgg gtg ggg    1296
Leu Phe Ser His Pro Ser Arg Met Pro Val Tyr Pro Lys Trp Val Gly
            420                 425                 430 gcc gac cat gca gat gac att cag tac gtt ttc ggg aag ccc ttc gcc    1344
Ala Asp His Ala Asp Asp Ile Gln Tyr Val Phe Gly Lys Pro Phe Ala
        435                 440                 445 acc ccc acg ggc tac cgg ccc caa gac agg aca gtc tct aag gcc atg    1392
Thr Pro Thr Gly Tyr Arg Pro Gln Asp Arg Thr Val Ser Lys Ala Met
450                 455                 460
```

-continued

```
atc gcc tac tgg acc aac ttt gcc aaa aca ggg gac ccc aac atg ggc      1440
Ile Ala Tyr Trp Thr Asn Phe Ala Lys Thr Gly Asp Pro Asn Met Gly
465                 470                 475                 480 gac tcg gct gtg ccc aca cac tgg gaa ccc tac act acg gaa aac agc      1488
Asp Ser Ala Val Pro Thr His Trp Glu Pro Tyr Thr Thr Glu Asn Ser
                485                 490                 495 ggc tac ctg gag atc acc aag aag atg ggc agc agc tcc atg aag cgg      1536
Gly Tyr Leu Glu Ile Thr Lys Lys Met Gly Ser Ser Ser Met Lys Arg
            500                 505                 510 agc ctg aga acc aac ttc ctg cgc tac tgg acc ctc acc tat ctg gcg      1584
Ser Leu Arg Thr Asn Phe Leu Arg Tyr Trp Thr Leu Thr Tyr Leu Ala
        515                 520                 525 ctg ccc aca gtg acc gac cag gag gcc acc cct gtg ccc ccc aca ggg      1632
Leu Pro Thr Val Thr Asp Gln Glu Ala Thr Pro Val Pro Pro Thr Gly
    530                 535                 540 gac tcc gag gcc act ccc gtg ccc ccc acg ggt gac tcc gag acc gcc      1680
Asp Ser Glu Ala Thr Pro Val Pro Pro Thr Gly Asp Ser Glu Thr Ala
545                 550                 555                 560 ccc gtg ccg ccc acg ggc gac tcc ggg gcc ccc ccc gtg ccg ccc acg      1728
Pro Val Pro Pro Thr Gly Asp Ser Gly Ala Pro Pro Val Pro Pro Thr
                565                 570                 575 ggt gac tcc ggg gcc ccc cct gtg ccc ccc acg ggt gac tct gag gct      1776
Gly Asp Ser Gly Ala Pro Pro Val Pro Pro Thr Gly Asp Ser Glu Ala
            580                 585                 590 gcc cct gtg ccc ccc aca ggt gac tcc aag gaa gct cag atg cct gca      1824
Ala Pro Val Pro Pro Thr Gly Asp Ser Lys Glu Ala Gln Met Pro Ala
        595                 600                 605 gtc att agg ttt tag                                                  1839
Val Ile Arg Phe
    610

<210> SEQ ID NO 11
<211> LENGTH: 612
<212> TYPE: PRT
<213> ORGANISM: Homo sapiens

<400> SEQUENCE: 11

Ala Lys Leu Gly Ala Val Tyr Thr Glu Gly Gly Phe Val Glu Gly Val
1               5                   10                  15

Asn Lys Lys Leu Gly Leu Gly Asp Ser Val Asp Ile Phe Lys Gly
            20                  25                  30

Ile Pro Phe Ala Ala Pro Thr Lys Ala Leu Glu Asn Pro Gln Pro His
        35                  40                  45

Pro Gly Trp Gln Gly Thr Leu Lys Ala Lys Asn Phe Lys Lys Arg Cys
    50                  55                  60

Leu Gln Ala Thr Ile Thr Gln Asp Ser Thr Tyr Gly Asp Glu Asp Cys
65                  70                  75                  80

Leu Tyr Leu Asn Ile Trp Val Pro Gln Gly Arg Lys Gln Val Ser Arg
                85                  90                  95

Asp Leu Pro Val Met Ile Trp Ile Tyr Gly Gly Ala Phe Leu Met Gly
            100                 105                 110

Ser Gly His Gly Ala Asn Phe Leu Asn Asn Tyr Leu Tyr Asp Gly Glu
        115                 120                 125

Glu Ile Ala Thr Arg Gly Asn Val Ile Val Val Thr Phe Asn Tyr Arg
    130                 135                 140

Val Gly Pro Leu Gly Phe Leu Ser Thr Gly Asp Ala Asn Leu Pro Gly
145                 150                 155                 160
```

-continued

```
Asn Tyr Gly Leu Arg Asp Gln His Met Ala Ile Ala Trp Val Lys Arg
            165                 170                 175

Asn Ile Ala Ala Phe Gly Gly Asp Pro Asn Asn Ile Thr Leu Phe Gly
            180                 185                 190

Glu Ser Ala Gly Gly Ala Ser Val Ser Leu Gln Thr Leu Ser Pro Tyr
            195                 200                 205

Asn Lys Gly Leu Ile Arg Arg Ala Ile Ser Gln Ser Gly Val Ala Leu
            210                 215                 220

Ser Pro Trp Val Ile Gln Lys Asn Pro Leu Phe Trp Ala Lys Lys Val
225                 230                 235                 240

Ala Glu Lys Val Gly Cys Pro Val Gly Asp Ala Ala Arg Met Ala Gln
            245                 250                 255

Cys Leu Lys Val Thr Asp Pro Arg Ala Leu Thr Leu Ala Tyr Lys Val
            260                 265                 270

Pro Leu Ala Gly Leu Glu Tyr Pro Met Leu His Tyr Val Gly Phe Val
            275                 280                 285

Pro Val Ile Asp Gly Asp Phe Ile Pro Ala Asp Pro Ile Asn Leu Tyr
            290                 295                 300

Ala Asn Ala Ala Asp Ile Asp Tyr Ile Ala Gly Thr Asn Asn Met Asp
305                 310                 315                 320

Gly His Ile Phe Ala Ser Ile Asp Met Pro Ala Ile Asn Lys Gly Asn
            325                 330                 335

Lys Lys Val Thr Glu Glu Asp Phe Tyr Lys Leu Val Ser Glu Phe Thr
            340                 345                 350

Ile Thr Lys Gly Leu Arg Gly Ala Lys Thr Thr Phe Asp Val Tyr Thr
            355                 360                 365

Glu Ser Trp Ala Gln Asp Pro Ser Gln Glu Asn Lys Lys Lys Thr Val
            370                 375                 380

Val Asp Phe Glu Thr Asp Val Leu Phe Leu Val Pro Thr Glu Ile Ala
385                 390                 395                 400

Leu Ala Gln His Arg Ala Asn Ala Lys Ser Ala Lys Thr Tyr Ala Tyr
            405                 410                 415

Leu Phe Ser His Pro Ser Arg Met Pro Val Tyr Pro Lys Trp Val Gly
            420                 425                 430

Ala Asp His Ala Asp Asp Ile Gln Tyr Val Phe Gly Lys Pro Phe Ala
            435                 440                 445

Thr Pro Thr Gly Tyr Arg Pro Gln Asp Arg Thr Val Ser Lys Ala Met
            450                 455                 460

Ile Ala Tyr Trp Thr Asn Phe Ala Lys Thr Gly Asp Pro Asn Met Gly
465                 470                 475                 480

Asp Ser Ala Val Pro Thr His Trp Glu Pro Tyr Thr Thr Glu Asn Ser
            485                 490                 495

Gly Tyr Leu Glu Ile Thr Lys Lys Met Gly Ser Ser Met Lys Arg
            500                 505                 510

Ser Leu Arg Thr Asn Phe Leu Arg Tyr Trp Thr Leu Thr Tyr Leu Ala
            515                 520                 525

Leu Pro Thr Val Thr Asp Gln Glu Ala Thr Pro Val Pro Pro Thr Gly
            530                 535                 540

Asp Ser Glu Ala Thr Pro Val Pro Pro Thr Gly Asp Ser Glu Thr Ala
545                 550                 555                 560

Pro Val Pro Pro Thr Gly Asp Ser Gly Ala Pro Pro Val Pro Pro Thr
            565                 570                 575
```

```
Gly Asp Ser Gly Ala Pro Pro Val Pro Pro Thr Gly Asp Ser Glu Ala
            580                 585                 590

Ala Pro Val Pro Pro Thr Gly Asp Ser Lys Glu Ala Gln Met Pro Ala
        595                 600                 605

Val Ile Arg Phe
    610

<210> SEQ ID NO 12
<211> LENGTH: 750
<212> TYPE: DNA
<213> ORGANISM: Homo sapiens
<220> FEATURE:
<221> NAME/KEY: CDS
<222> LOCATION: (1)..(747)

<400> SEQUENCE: 12 ttt gat gtc tac acc gag tcc tgg gcc cag gac cca tcc cag gag aat        48
Phe Asp Val Tyr Thr Glu Ser Trp Ala Gln Asp Pro Ser Gln Glu Asn
1               5                  10                  15 aag aag aag act gtg gtg gac ttt gag acc gat gtc ctc ttc ctg gtg        96
Lys Lys Lys Thr Val Val Asp Phe Glu Thr Asp Val Leu Phe Leu Val
            20                  25                  30 ccc acc gag att gcc cta gcc cag cac aga gcc aat gcc aag agt gcc       144
Pro Thr Glu Ile Ala Leu Ala Gln His Arg Ala Asn Ala Lys Ser Ala
        35                  40                  45 aag acc tac gcc tac ctg ttt tcc cat ccc tct cgg atg ccc gtc tac       192
Lys Thr Tyr Ala Tyr Leu Phe Ser His Pro Ser Arg Met Pro Val Tyr
    50                  55                  60 ccc aaa tgg gtg ggg gcc gac cat gca gat gac att cag tac gtt ttc       240
Pro Lys Trp Val Gly Ala Asp His Ala Asp Asp Ile Gln Tyr Val Phe
65                  70                  75                  80 ggg aag ccc ttc gcc acc ccc acg ggc tac cgg ccc caa gac agg aca       288
Gly Lys Pro Phe Ala Thr Pro Thr Gly Tyr Arg Pro Gln Asp Arg Thr
                85                  90                  95 gtc tct aag gcc atg atc gcc tac tgg acc aac ttt gcc aaa aca ggg       336
Val Ser Lys Ala Met Ile Ala Tyr Trp Thr Asn Phe Ala Lys Thr Gly
            100                 105                 110 gac ccc aac atg ggc gac tcg gct gtg ccc aca cac tgg gaa ccc tac       384
Asp Pro Asn Met Gly Asp Ser Ala Val Pro Thr His Trp Glu Pro Tyr
        115                 120                 125 act acg gaa aac agc ggc tac ctg gag atc acc aag aag atg ggc agc       432
Thr Thr Glu Asn Ser Gly Tyr Leu Glu Ile Thr Lys Lys Met Gly Ser
    130                 135                 140 agc tcc atg aag cgg agc ctg aga acc aac ttc ctg cgc tac tgg acc       480
Ser Ser Met Lys Arg Ser Leu Arg Thr Asn Phe Leu Arg Tyr Trp Thr
145                 150                 155                 160 ctc acc tat ctg gcg ctg ccc aca gtg acc gac cag gag gcc acc cct       528
Leu Thr Tyr Leu Ala Leu Pro Thr Val Thr Asp Gln Glu Ala Thr Pro
                165                 170                 175 gtg ccc ccc aca ggg gac tcc gag gcc act ccc gtg ccc ccc acg ggt       576
Val Pro Pro Thr Gly Asp Ser Glu Ala Thr Pro Val Pro Pro Thr Gly
            180                 185                 190 gac tcc gag acc gcc ccc gtg ccg ccc acg ggc gac tcc ggg gcc ccc       624
Asp Ser Glu Thr Ala Pro Val Pro Pro Thr Gly Asp Ser Gly Ala Pro
        195                 200                 205 ccc gtg ccg ccc acg ggt gac tcc ggg gcc ccc cct gtg ccc ccc acg       672
Pro Val Pro Pro Thr Gly Asp Ser Gly Ala Pro Pro Val Pro Pro Thr
    210                 215                 220
```

```
ggt gac tct gag gct gcc cct gtg ccc cca aca ggt gac tcc aag gaa    720
Gly Asp Ser Glu Ala Ala Pro Val Pro Pro Thr Gly Asp Ser Lys Glu
225                 230                 235                 240 gct cag atg cct gca gtc att agg ttt tag                            750
Ala Gln Met Pro Ala Val Ile Arg Phe
                245
```

<210> SEQ ID NO 13
<211> LENGTH: 249
<212> TYPE: PRT
<213> ORGANISM: Homo sapiens

<400> SEQUENCE: 13

```
Phe Asp Val Tyr Thr Glu Ser Trp Ala Gln Asp Pro Ser Gln Glu Asn
1               5                   10                  15

Lys Lys Lys Thr Val Val Asp Phe Glu Thr Asp Val Leu Phe Leu Val
                20                  25                  30

Pro Thr Glu Ile Ala Leu Ala Gln His Arg Ala Asn Ala Lys Ser Ala
            35                  40                  45

Lys Thr Tyr Ala Tyr Leu Phe Ser His Pro Ser Arg Met Pro Val Tyr
        50                  55                  60

Pro Lys Trp Val Gly Ala Asp His Ala Asp Asp Ile Gln Tyr Val Phe
65                  70                  75                  80

Gly Lys Pro Phe Ala Thr Pro Thr Gly Tyr Arg Pro Gln Asp Arg Thr
                85                  90                  95

Val Ser Lys Ala Met Ile Ala Tyr Trp Thr Asn Phe Ala Lys Thr Gly
            100                 105                 110

Asp Pro Asn Met Gly Asp Ser Ala Val Pro Thr His Trp Glu Pro Tyr
        115                 120                 125

Thr Thr Glu Asn Ser Gly Tyr Leu Glu Ile Thr Lys Lys Met Gly Ser
130                 135                 140

Ser Ser Met Lys Arg Ser Leu Arg Thr Asn Phe Leu Arg Tyr Trp Thr
145                 150                 155                 160

Leu Thr Tyr Leu Ala Leu Pro Thr Val Thr Asp Gln Glu Ala Thr Pro
                165                 170                 175

Val Pro Pro Thr Gly Asp Ser Glu Ala Thr Pro Val Pro Pro Thr Gly
            180                 185                 190

Asp Ser Glu Thr Ala Pro Val Pro Pro Thr Gly Asp Ser Gly Ala Pro
        195                 200                 205

Pro Val Pro Pro Thr Gly Asp Ser Gly Ala Pro Pro Val Pro Pro Thr
210                 215                 220

Gly Asp Ser Glu Ala Ala Pro Val Pro Pro Thr Gly Asp Ser Lys Glu
225                 230                 235                 240

Ala Gln Met Pro Ala Val Ile Arg Phe
                245
```

<210> SEQ ID NO 14
<211> LENGTH: 11
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Glu or Gly
<220> FEATURE:
<221> NAME/KEY: MISC_FEATURE
<222> LOCATION: (11)..(11)
<223> OTHER INFORMATION: Xaa is Glu or Gly -continued

```
<400> SEQUENCE: 14

Asp Ser Xaa Ala Pro Pro Val Pro Pro Thr Xaa
1               5                   10
```